US 8,758,762 B2

(12) United States Patent
Kim et al.

(10) Patent No.: US 8,758,762 B2
(45) Date of Patent: Jun. 24, 2014

(54) METHOD FOR PREPARING RECOMBINANT ANTIGEN COMPLEX USING ROTAVIRUS NANOPARTICLE

(75) Inventors: Won Yong Kim, Seoul (KR); In Sik Chung, Seoul (KR); Jong-Bum Kim, Suwon-si (KR); Dong-Hwa Shon, Seongnam-si (KR); Van Thai Than, Seoul (KR); Jang Won Yoon, Anyang-si (KR); Joo Hyoung Park, Seoul (KR); In-Hyuk Baek, Incheon (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 147 days.

(21) Appl. No.: 13/095,303

(22) Filed: Apr. 27, 2011

(65) Prior Publication Data

US 2011/0311573 A1    Dec. 22, 2011

(30) Foreign Application Priority Data

Apr. 30, 2010 (KR) ........................ 10-2010-0041095

(51) Int. Cl.
*A61K 39/00* (2006.01)
*A61K 39/12* (2006.01)
*A61K 39/29* (2006.01)
*G01N 33/569* (2006.01)

(52) U.S. Cl.
CPC .......... *A61K 39/29* (2013.01); *G01N 33/56983* (2013.01); *A61K 2039/5258* (2013.01); *G01N 2333/14* (2013.01)
USPC .................. 424/184.1; 424/204.1; 424/226.1

(58) Field of Classification Search
USPC .......................................... 424/196
See application file for complete search history.

(56) References Cited

U.S. PATENT DOCUMENTS

2007/0207526 A1*  9/2007  Coit et al. .................... 435/91.1

OTHER PUBLICATIONS

Bányai et al., "Molecular Characterization of a Rare, Human-Porcine Reassortant Rotavirus Strain, G11P[6], from Ecuador," Arch. Virol. 154:1823-1829, 2009.
Estes et al., "Rotavirus Gene Structure and Function," Microbiol. Rev. 53:410-449, 1989.
Gust, "Epidemiological Patterns of Hepatitis A in Different Parts of the World," Vaccine 10 (Suppl. 1):S56-SS58, 1992.
Totsuka et al., "Hepatitis A Virus Proteins," Intervirology 42:63-68, 1999.

* cited by examiner

*Primary Examiner* — Zachariah Lucas
*Assistant Examiner* — Barry A Chestnut
(74) *Attorney, Agent, or Firm* — Clark & Elbing LLP

(57) ABSTRACT

Disclosed are a construct for expressing a rotavirus antigen complex loaded with a heterologous virus epitope, a vaccine composition containing the rotavirus antigen complex, a virus-like particle of rotavirus containing the rotavirus antigen complex, and a vaccine composition containing the virus-like particle of rotavirus. According to the present disclosure, an antigen complex containing a rotavirus antigen as well as a heterologous virus epitope and a virus-like particle of rotavirus containing the antigen complex can be produced in large scale at low cost. Thus, the present disclosure may be applied for research and development of novel complex vaccines for rotavirus and heterologous virus.

5 Claims, 16 Drawing Sheets
(4 of 16 Drawing Sheet(s) Filed in Color)

SEQUENCE LISTING

```
<160> NUMBER OF SEQ ID NOS: 12

<210> SEQ ID NO 1
<211> LENGTH: 325
<212> TYPE: PRT
<213> ORGANISM: Human Rotavirus

<400> SEQUENCE: 1

Tyr Gly Ile Glu Tyr Thr Thr Ile Leu Ile Phe Leu Ile Ser Ile Ile
1               5                   10                  15

Leu Leu Asn Tyr Ile Leu Lys Ser Val Thr Arg Ile Met Asp Tyr Ile
            20                  25                  30

Ile Tyr Arg Phe Leu Leu Ile Thr Val Ala Leu Phe Ala Leu Thr Arg
        35                  40                  45

Ala Gln Asn Tyr Gly Leu Asn Leu Pro Ile Thr Gly Ser Met Asp Ala
    50                  55                  60

Val Tyr Thr Asn Ser Thr Gln Glu Glu Val Phe Leu Thr Ser Thr Leu
65                  70                  75                  80

Cys Leu Tyr Tyr Pro Thr Glu Val Ser Thr Gln Ile Asn Asp Gly Asp
                85                  90                  95

Trp Lys Asp Ser Leu Ser Gln Met Phe Leu Thr Lys Gly Trp Pro Thr
            100                 105                 110

Gly Ser Val Tyr Phe Lys Glu Tyr Ser Asn Ile Val Asp Ser Ser Val
        115                 120                 125

Asp Pro Gln Leu Tyr Cys Asp Tyr Asn Leu Val Leu Met Lys Tyr Asn
    130                 135                 140

Gln Ser Leu Lys Leu Asp Met Ser Glu Leu Ala Asp Leu Ile Leu Asn
145                 150                 155                 160

Glu Trp Leu Cys Asn Pro Met Asp Val Thr Leu Tyr Tyr Gln Gln
                165                 170                 175

Ser Gly Glu Ser Asn Lys Trp Ile Ser Met Gly Ser Ser Cys Thr Val
            180                 185                 190

Lys Val Cys Pro Leu Asn Thr Gln Thr Leu Gly Ile Gly Cys Gln Thr
```

```
                195                 200                 205
Thr Asn Val Asp Ser Phe Glu Thr Ile Ala Glu Asn Glu Lys Leu Ala
    210                 215                 220

Ile Val Asp Val Val Asp Gly Ile Asn His Lys Ile Asn Leu Thr Thr
225                 230                 235                 240

Thr Thr Cys Thr Ile Arg Asn Cys Lys Lys Leu Gly Pro Arg Glu Asn
                245                 250                 255

Val Ala Val Ile Gln Val Gly Gly Pro Asn Val Leu Asp Ile Thr Ala
            260                 265                 270

Asp Ser Thr Thr Asn Pro Gln Ile Glu Arg Met Met Arg Val Asn Trp
        275                 280                 285

Lys Lys Trp Trp Gln Val Phe Tyr Thr Ile Val Asp Tyr Ile Asn Gln
    290                 295                 300

Ile Val Gln Val Met Ser Lys Arg Ser Arg Ser Leu Asn Ser Ala Ala
305                 310                 315                 320

Phe Tyr Tyr Arg Val
            325

<210> SEQ ID NO 2
<211> LENGTH: 77
<212> TYPE: PRT
<213> ORGANISM: Hepatitis A Virus

<400> SEQUENCE: 2

Met Asp Leu Lys Ser Ser Val Asp Asp Pro Arg Ser Glu Glu Asp Arg
1               5                   10                  15

Arg Phe Glu Ser His Ile Glu Cys Arg Lys Pro Tyr Arg Glu Leu Arg
            20                  25                  30

Leu Glu Val Gly Lys Ser Arg Leu Lys Tyr Ala Gln Glu Glu Leu Ser
        35                  40                  45

Asn Glu Val Leu Pro Pro Arg Lys Met Lys Gly Leu Phe Ser Gln
    50                  55                  60

Ala Lys Ile Ser Leu Phe Tyr Thr Glu Glu His Glu Ile
65                  70                  75

<210> SEQ ID NO 3
<211> LENGTH: 55
<212> TYPE: PRT
<213> ORGANISM: Hepatitis A Virus

<400> SEQUENCE: 3

Met Lys Gln Asn Met Ser Glu Phe Met Glu Leu Trp Ser Gln Gly Val
1               5                   10                  15

Ser Asp Asp Asp Asn Asp Ser Ala Val Ala Glu Phe Phe Gln Ser Phe
            20                  25                  30

Pro Ser Gly Glu Pro Ser Asn Ser Lys Leu Ser Ser Phe Phe Gln Ser
        35                  40                  45

Val Thr Asn His Lys Trp Val
    50                  55

<210> SEQ ID NO 4
<211> LENGTH: 890
<212> TYPE: PRT
<213> ORGANISM: Human Rotavirus

<400> SEQUENCE: 4

Met Ala Tyr Arg Lys Arg Gly Ala Lys Arg Glu Asn Leu Pro Gln Gln
1               5                   10                  15
```

```
Asn Glu Arg Leu Gln Glu Lys Glu Ile Glu Lys Asp Val Asp Val Thr
             20                  25                  30

Met Glu Asn Lys Asn Asn Arg Lys Gln Gln Leu Ser Asp Lys Val
         35                  40                  45

Leu Ser Gln Lys Glu Ile Ile Thr Asp Ala Gln Asp Ile Lys
 50                  55                  60

Ile Ala Gly Glu Ile Lys Lys Ser Ser Lys Glu Glu Ser Lys Gln Leu
 65                  70                  75                  80

Leu Glu Ile Leu Lys Thr Lys Glu Asp His Gln Lys Glu Ile Gln Tyr
                 85                  90                  95

Glu Ile Leu Gln Lys Thr Ile Pro Thr Phe Glu Ser Lys Glu Ser Ile
            100                 105                 110

Leu Lys Lys Leu Glu Asp Ile Arg Pro Glu Gln Ala Lys Lys Gln Met
        115                 120                 125

Lys Leu Phe Arg Ile Phe Glu Pro Lys Gln Leu Pro Ile Tyr Arg Ala
130                 135                 140

Asn Gly Glu Lys Glu Leu Arg Asn Arg Trp Tyr Trp Lys Leu Lys Lys
145                 150                 155                 160

Asp Thr Leu Pro Asp Gly Asp Tyr Asp Val Arg Glu Tyr Phe Leu Asn
                165                 170                 175

Leu Tyr Asp Gln Ile Leu Ile Glu Met Pro Asp Tyr Leu Leu Leu Lys
            180                 185                 190

Asp Met Ala Val Glu Asn Lys Asn Ser Arg Asp Ala Gly Lys Val Val
        195                 200                 205

Asp Ser Glu Thr Ala Asn Ile Cys Asp Ala Ile Phe Gln Asp Glu Glu
    210                 215                 220

Thr Glu Gly Val Val Arg Arg Phe Ile Ala Asp Met Arg Gln Gln Val
225                 230                 235                 240

Gln Ala Asp Arg Asn Ile Val Asn Tyr Pro Ser Ile Leu His Pro Ile
                245                 250                 255

Asp His Ala Phe Asn Glu Tyr Phe Leu Asn His Gln Leu Val Glu Pro
            260                 265                 270

Leu Asn Asn Glu Ile Ile Phe Asn Tyr Ile Pro Glu Arg Ile Arg Asn
        275                 280                 285

Asp Val Asn Tyr Ile Leu Asn Met Asp Met Asn Leu Pro Ser Thr Ala
    290                 295                 300

Arg Tyr Ile Arg Pro Asn Leu Leu Gln Asp Arg Leu Asn Leu His Asp
305                 310                 315                 320

Asn Phe Glu Ser Leu Trp Asp Thr Ile Thr Thr Ser Asn Tyr Ile Leu
                325                 330                 335

Ala Arg Ser Val Val Pro Asp Leu Lys Glu Lys Glu Leu Val Ser Thr
            340                 345                 350

Glu Ala Gln Ile Gln Lys Met Ser Gln Asp Leu Gln Leu Glu Ala Leu
        355                 360                 365

Thr Ile Gln Ser Glu Thr Gln Phe Leu Ala Gly Ile Asn Ser Gln Ala
    370                 375                 380

Ala Asn Asp Cys Phe Lys Thr Leu Ile Ala Ala Met Leu Ser Gln Arg
385                 390                 395                 400

Thr Met Ser Leu Asp Phe Val Thr Thr Asn Tyr Met Ser Leu Ile Ser
                405                 410                 415

Gly Met Trp Leu Leu Thr Val Ile Pro Asn Asp Met Phe Leu Arg Glu
            420                 425                 430
```

```
Ser Leu Val Ala Cys Glu Leu Ala Ile Ile Asn Thr Ile Val Tyr Pro
            435                 440                 445

Ala Phe Gly Met Gln Arg Met His Tyr Arg Asn Gly Asp Pro Gln Thr
450                 455                 460

Pro Phe Gln Ile Ala Glu Gln Gln Ile Gln Asn Phe Gln Val Ala Asn
465                 470                 475                 480

Trp Leu His Phe Ile Asn Asn Asn Arg Phe Arg Gln Val Val Ile Asp
                485                 490                 495

Gly Val Leu Asn Gln Thr Leu Asn Asp Asn Ile Arg Asn Gly Gln Val
            500                 505                 510

Ile Asn Gln Leu Met Glu Ala Leu Met Gln Leu Ser Arg Gln Gln Phe
            515                 520                 525

Pro Thr Met Pro Val Asp Tyr Lys Arg Ser Ile Gln Arg Gly Ile Leu
530                 535                 540

Leu Leu Ser Asn Arg Leu Gly Gln Leu Val Asp Leu Thr Arg Leu Val
545                 550                 555                 560

Ser Tyr Asn Tyr Glu Thr Leu Met Ala Cys Val Thr Met Asn Met Gln
                565                 570                 575

His Val Gln Thr Leu Thr Thr Glu Lys Leu Gln Leu Thr Ser Val Thr
            580                 585                 590

Ser Leu Cys Met Leu Ile Gly Asn Thr Thr Val Ile Pro Ser Pro Gln
            595                 600                 605

Thr Leu Phe His Tyr Tyr Asn Ile Asn Val Asn Phe His Ser Asn Tyr
            610                 615                 620

Asn Glu Arg Ile Asn Asp Ala Val Ala Ile Ile Thr Ala Ala Asn Arg
625                 630                 635                 640

Leu Asn Leu Tyr Gln Lys Lys Met Lys Ser Ile Val Glu Asp Phe Leu
                645                 650                 655

Lys Arg Leu Gln Ile Phe Asp Val Pro Arg Val Pro Asp Asp Gln Met
            660                 665                 670

Tyr Arg Leu Arg Asp Arg Leu Arg Leu Leu Pro Val Glu Arg Arg Arg
            675                 680                 685

Leu Asp Ile Phe Asn Leu Ile Leu Met Asn Met Glu Gln Ile Glu Arg
690                 695                 700

Ala Ser Asp Lys Ile Ala Gln Gly Val Ile Ile Ala Tyr Arg Asp Met
705                 710                 715                 720

Gln Leu Glu Arg Asp Glu Met Tyr Gly Tyr Val Asn Ile Ala Arg Asn
                725                 730                 735

Leu Asp Gly Tyr Gln Gln Ile Asn Leu Glu Glu Leu Met Arg Thr Gly
            740                 745                 750

Asp Tyr Gly Gln Ile Thr Asn Met Leu Leu Asn Asn Gln Pro Val Ala
            755                 760                 765

Leu Val Gly Ala Leu Pro Phe Val Thr Asp Ser Ser Val Ile Ser Leu
770                 775                 780

Ile Ala Lys Leu Asp Ala Thr Val Phe Ala Gln Ile Val Lys Leu Arg
785                 790                 795                 800

Lys Val Asp Thr Leu Lys Pro Ile Leu Tyr Lys Ile Asn Ser Asp Ser
                805                 810                 815

Asn Asp Phe Tyr Leu Val Ala Asn Tyr Asp Trp Ile Pro Thr Ser Thr
            820                 825                 830

Thr Lys Val Tyr Lys Gln Val Pro Gln Pro Phe Asp Phe Arg Ala Ser
            835                 840                 845

Met His Met Leu Thr Ser Asn Leu Thr Phe Thr Val Tyr Ser Asp Leu
```

```
                   850                 855                 860
Leu Ser Phe Val Ser Ala Asp Thr Val Glu Pro Ile Asn Ala Val Ala
865                 870                 875                 880

Phe Asp Asn Met Arg Ile Met Asn Glu Leu
                885                 890

<210> SEQ ID NO 5
<211> LENGTH: 775
<212> TYPE: PRT
<213> ORGANISM: Human Rotavirus

<400> SEQUENCE: 5

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
                20                  25                  30

Val Thr Ile Asn Pro Ser Pro Phe Ala Gln Thr Arg Tyr Ala Pro Val
            35                  40                  45

Asn Trp Gly His Gly Glu Ile Asn Asp Ser Thr Thr Val Glu Pro Met
        50                  55                  60

Leu Asp Gly Pro Tyr Gln Pro Thr Thr Phe Thr Pro Pro Asn Asp Tyr
65                  70                  75                  80

Trp Ile Leu Ile Asn Ser Asn Thr Asn Gly Val Val Tyr Glu Ser Thr
                85                  90                  95

Asn Asn Ser Asp Phe Trp Thr Ala Val Val Ala Ile Glu Pro His Val
                100                 105                 110

Asn Pro Val Asp Arg Gln Tyr Thr Ile Phe Gly Glu Ser Lys Gln Phe
            115                 120                 125

Asn Val Ser Asn Asp Ser Asn Lys Trp Lys Phe Leu Glu Met Phe Arg
        130                 135                 140

Ser Ser Ser Gln Asn Glu Phe Tyr Asn Arg Arg Thr Leu Thr Ser Asp
145                 150                 155                 160

Thr Arg Phe Val Gly Ile Leu Lys Tyr Gly Gly Arg Val Trp Thr Phe
                165                 170                 175

His Gly Glu Thr Pro Arg Ala Thr Thr Asp Ser Ser Ser Thr Ala Asn
                180                 185                 190

Leu Asn Asn Ile Ser Ile Thr Ile His Ser Glu Phe Tyr Ile Ile Pro
            195                 200                 205

Arg Ser Gln Glu Ser Lys Cys Asn Glu Tyr Ile Asn Asn Gly Leu Pro
        210                 215                 220

Pro Ile Gln Asn Thr Arg Asn Val Val Pro Leu Pro Leu Ser Ser Arg
225                 230                 235                 240

Ser Ile Gln Tyr Lys Arg Ala Gln Val Asn Glu Asp Ile Ile Val Ser
                245                 250                 255

Lys Thr Ser Leu Trp Lys Glu Met Gln Tyr Asn Arg Asp Ile Ile Ile
                260                 265                 270

Arg Phe Lys Phe Gly Asn Ser Ile Val Lys Met Gly Gly Leu Gly Tyr
            275                 280                 285

Lys Trp Ser Glu Ile Ser Tyr Lys Ala Ala Asn Tyr Gln Tyr Asn Tyr
        290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Phe Leu Pro Thr Asp Phe
                325                 330                 335
```

-continued

```
Gly Ile Ser Arg Tyr Glu Val Ile Lys Asn Ser Tyr Val Tyr Val
                340                 345                 350
Asp Tyr Trp Asp Asp Ser Lys Ala Phe Arg Asn Met Val Tyr Val Arg
            355                 360                 365
Ser Leu Ala Ala Asn Leu Asn Ser Val Lys Cys Thr Gly Gly Ser Tyr
        370                 375                 380
Asn Phe Ser Ile Pro Val Gly Ala Trp Pro Val Met Asn Gly Gly Ala
385                 390                 395                 400
Val Ser Leu His Phe Ala Gly Val Thr Leu Ser Thr Gln Phe Thr Asp
                405                 410                 415
Phe Val Ser Leu Asn Ser Leu Arg Phe Arg Phe Ser Leu Thr Val Asp
            420                 425                 430
Glu Pro Pro Phe Ser Ile Leu Arg Thr Arg Thr Val Asn Leu Tyr Gly
        435                 440                 445
Leu Pro Ala Ala Asn Pro Asn Gly Asn Glu Tyr Tyr Glu Ile Ser
        450                 455                 460
Gly Arg Phe Ser Leu Ile Tyr Leu Val Pro Thr Asn Asp Asp Tyr Gln
465                 470                 475                 480
Thr Pro Ile Met Asn Ser Val Thr Val Arg Gln Asp Leu Glu Arg Gln
                485                 490                 495
Leu Thr Asp Leu Arg Glu Glu Phe Asn Ser Leu Ser Gln Glu Ile Ala
            500                 505                 510
Met Ala Gln Leu Ile Asp Leu Ala Leu Leu Pro Leu Asp Met Phe Ser
        515                 520                 525
Met Phe Ser Gly Ile Lys Ser Thr Ile Asp Leu Thr Lys Ser Met Ala
        530                 535                 540
Thr Ser Val Met Lys Lys Phe Arg Lys Ser Lys Leu Ala Thr Ser Ile
545                 550                 555                 560
Ser Glu Met Thr Asn Ser Leu Ser Asp Ala Ala Ser Ala Ser Arg
                565                 570                 575
Asn Val Ser Ile Arg Ser Asn Leu Ser Ala Ile Ser Asn Trp Thr Asn
            580                 585                 590
Val Ser Asn Asp Val Ser Asn Val Thr Asn Ser Leu Asn Asp Ile Ser
        595                 600                 605
Thr Gln Thr Ser Thr Ile Ser Lys Lys Phe Arg Leu Lys Glu Met Ile
        610                 615                 620
Thr Gln Thr Glu Gly Met Ser Phe Asp Asp Ile Ser Ala Ala Val Leu
625                 630                 635                 640
Lys Thr Lys Ile Asp Met Ser Thr Gln Ile Gly Lys Asn Thr Leu Pro
                645                 650                 655
Asp Ile Val Thr Glu Ala Ser Glu Lys Phe Ile Pro Lys Arg Ser Tyr
            660                 665                 670
Arg Ile Leu Lys Asp Asp Glu Val Met Glu Ile Asn Thr Glu Gly Lys
        675                 680                 685
Phe Phe Ala Tyr Lys Ile Asn Thr Phe Asp Glu Val Pro Phe Asp Val
        690                 695                 700
Asn Lys Phe Ala Glu Leu Val Thr Asp Ser Pro Val Ile Ser Ala Ile
705                 710                 715                 720
Ile Asp Phe Lys Thr Leu Lys Asn Leu Asn Asp Asn Tyr Gly Ile Thr
                725                 730                 735
Arg Thr Glu Ala Leu Asn Leu Ile Lys Ser Asn Pro Asn Met Leu Arg
            740                 745                 750
Asn Phe Ile Asn Gln Asn Asn Pro Ile Ile Arg Asn Arg Ile Glu Gln
```

```
                755                 760                 765
Leu Ile Leu Gln Cys Lys Leu
    770                 775

<210> SEQ ID NO 6
<211> LENGTH: 397
<212> TYPE: PRT
<213> ORGANISM: Human Rotavirus

<400> SEQUENCE: 6

Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Val Thr Met Asn Gly Asn Asp Phe Gln Thr
        35                  40                  45

Gly Gly Ile Gly Asn Leu Pro Val Arg Asn Trp Thr Phe Asp Phe Gly
    50                  55                  60

Leu Leu Gly Thr Thr Leu Leu Asn Leu Asp Ala Asn Tyr Val Glu Asn
65                  70                  75                  80

Ala Arg Thr Ile Ile Glu Tyr Phe Ile Asp Phe Ile Asp Asn Val Cys
                85                  90                  95

Met Asp Glu Met Ala Arg Glu Ser Gln Arg Asn Gly Val Ala Pro Gln
            100                 105                 110

Ser Glu Ala Leu Arg Lys Leu Ala Gly Ile Lys Phe Lys Arg Ile Asn
        115                 120                 125

Phe Asp Asn Ser Ser Glu Tyr Ile Glu Asn Trp Leu Gln Asn Arg
    130                 135                 140

Arg Gln Arg Thr Gly Phe Val Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
            260                 265                 270

Tyr Gln Ala Arg Phe Gly Thr Ile Ile Ala Arg Asn Phe Asp Ala Ile
        275                 280                 285

Arg Leu Leu Phe Gln Leu Met Arg Pro Pro Asn Met Thr Pro Ala Val
    290                 295                 300

Asn Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350
```

```
Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395

<210> SEQ ID NO 7
<211> LENGTH: 975
<212> TYPE: DNA
<213> ORGANISM: Human Rotavirus

<400> SEQUENCE: 7
tatggtattg aatataccac aattctaatc tttttgatat caatcattct actcaactat      60
atattaaaat cagtgactcg aataatggac tacattatat atagattttt gttgattact     120
gtagcattat ttgctttgac aagagctcag aattatggac ttaacttacc aataacagga     180
tcaatggacg ctgtatatac taactctact caagaagaag tgtttctaac ttctacgtta     240
tgtctgtatt atccaactga agtaagtact caaatcaatg atggtgactg aaagactca     300 ttgtcgcaaa tgtttcttac aaaggggttgg ccaacaggat ctgtttactt taaagagtac    360
tcaaatattg ttgattcttc tgttgaccca cagctgtatt gtgactataa tttagtactt     420
atgaaatata accaaagtct taaattagat atgtcagagt tagctgattt aatattgaat     480
gaatggttat gtaacccaat ggatgtaaca ttatactatt atcaacaatc gggagaatca     540
aataagtgga tatcgatggg atcatcatgt accgtgaaag tgtgtccgct aaatacacaa     600
acgttaggga taggttgtca acaacaaac gtagactcat ttgaaacgat tgctgagaat     660
gagaaattag ctatagtgga tgtcgttgat gggataaatc ataaaataaa tttaacaact     720
acgacatgta ctattcgaaa ttgtaagaaa ttaggtccaa gagaaaatgt agctgtaata     780
caagttggtg gtcctaatgt gttagacata acagcagatt caacaactaa tccacaaatt     840
gagagaatga tgagagtgaa ttggaaaaag tggtggcaag tatttatac tatagtagat     900 tatattaatc aaattgtaca ggtaatgtcc aaaagatcaa gatcattaaa ttctgcagct     960
ttttattata gagta                                                     975

<210> SEQ ID NO 8
<211> LENGTH: 231
<212> TYPE: DNA
<213> ORGANISM: Hepatitis A Virus

<400> SEQUENCE: 8
atggacttga agtcatcagt ggatgatcct agatcagagg aggacagaag atttgagagt      60
catatagaat gtaggaaacc atacagagaa ttgagattgg aggttggtaa atcaagactc     120
aaatatgctc aggaagagtt gtcaaatgaa gtgcttccac ctcctaggaa aatgaagggg     180
ctattttcac aagctaagat ttctcttttt tacactgagg agcatgaaat a              231

<210> SEQ ID NO 9
<211> LENGTH: 165
<212> TYPE: DNA
<213> ORGANISM: Hepatitis A Virus

<400> SEQUENCE: 9
atgaaacaaa atatgagtga attcatggag ttgtggtctc agggagtttc agatgatgat      60
aatgatagtg cagtagctga gttttttcca actcttttcc atctggtgaa ccatcaaactct    120
```

```
aaattatcta gttttttcca atctgttact aatcacaagt gggtt            165
```

<210> SEQ ID NO 10
<211> LENGTH: 2673
<212> TYPE: DNA
<213> ORGANISM: Human Rotavirus

<400> SEQUENCE: 10

```
atggcgtaca ggaagcgcgg agctaaacgt gaaaacttac cacaacaaaa tgaacgtctg    60
caagaaaaag aaattgaaaa agatgtggat gtaactatgg agaataaaaa taacaataga   120
aagcagcaat tatctgataa agtactatca caaaaagagg aataataac tgatgcacaa    180
gatgatatta aatagctgg tgagattaaa aaatcatcaa agaagagtc aaaacagttg     240
ctcgaaatat taaaaacgaa agaagaccat cagaaagaaa tacagtatga aattctacaa    300
aaaacgatac cgacttttga atcaaaagaa tcaattttga aaaaattaga agatataaga   360
ccggagcaag ctaagaagca aatgaaattg tttagaatat ttgaaccaaa acaattacca    420
atctatcgag caaatggtga aaagaattg agaaatagag ggtattggaa attgaaaaag    480
gatacgctgc cagatggaga ttatgatgta cgagaatatt tcttaaattt atatgatcag    540
atcctgatag aaatgccaga ttatttgcta ctgaaagata tggctgtaga aaataaaaac    600
tctagagatg ctggtaaagt tgtagattct gaaacggcaa atatttgtga tgctatattt    660
caagatgaag agacagaggg agttgtcaga agattcattg cagatatgag acaacaggtt    720
caggctgata gaaatattgt caattatcca tcaattttac atccaattga tcacgcattt    780
aatgaatatt ttctaaatca tcaattagtc gaaccactaa ataatgaaat catttttaat    840
tatataccag aaagaataag gaatgatgtt aactatatt tgaatatgga tatgaatttg    900
ccatcaacag caagatatat tagaccaaat ttattgcaag atagactaaa tttacatgat    960
aattttgaat cattatggga cacaataact acatcaaatt atatactagc cagatcagtt   1020
gtgcctgatt tgaaggaaaa agaattagtt tcaactgaag ctcagataca gaaaatgtct   1080
caagatttgc aacttgaagc tttaacgata caatctgaaa cgcagtttct tgctggcata   1140
aattcacaag cagcaaatga ttgttttaaa acattgatag cagctatgtt aagccagcgt   1200
acaatgtcat tagattttgt aaccacgaat tatatgtcac ttatatctgg tatgtggcta   1260
ttgaccgtta taccaaatga tatgtttctt cgtgaatcat tagtcgcatg cgaattggcc   1320
ataataaata ctatagttta tccagcattt ggaatgcaaa gaatgcatta tagaaatggt   1380
gatcccaga ctccgtttca atagcagaaa cagcaaatac aaaattttca gtagctaat    1440
tggttacatt ttattaataa taatagattt aggcaagttg ttattgatgg agtgttaaat   1500
caaacactta acgataatat taggaatgga caagttatta atcagttaat ggaagcatta   1560
atgcagctat ctagacaaca atttccgact atgccagttg attataaaag atcaatccaa   1620
agaggaatat tactattatc taacagatta ggtcagttag ttgatttaac aagattagta   1680
tcatataatt atgaaactct aatggcttgt gtaactatga atatgcaaca tgttcaaact   1740
ctcactaccg aaaaattaca attaacttct gtcacatctt tatgtatgtt aattggaaat   1800
actacagtaa ttccaagtcc acaaacatta tttcactatt ataacataaa tgtaaatttt   1860
cattcaaatt ataacgaacg aattaacgac gcagtggcta tcattacggc tgctaataga   1920
ctaaacttat atcagaaaaa aatgaaatca atagttgagg attttttgaa aagattgcaa   1980
attttttgatg taccacgagt accagatgac caaatgtaca ggttgagaga tagacttagg   2040
ttattaccag ttgaaagacg aagacttgat atatttaatt taatattaat gaatatggag   2100
```

-continued

```
cagatcgaac gagcttcaga taaaattgct caaggagtaa taattgctta tagagatatg   2160
caactagaaa gagatgagat gtatggatat gtcaacattg ctagaaatct cgatggatat   2220
caacaaatta acctagagga gttgatgaga actggagact atgggcaaat tactaatatg   2280
ttattaaaca atcagcctgt agctttagta ggggcattac catttgtgac ggattcttca   2340
gttatatcac tcattgcaaa attagatgct acagttttg ctcaaatagt taaacttaga    2400
aaagtggaca ctttaaaacc aatattgtat aagataaatt ctgattctaa tgatttctac   2460
ttagttgcaa attatgattg gataccaact tcaaccacaa aagtctataa acaagtacca   2520
caaccttttg atttcagagc gtcaatgcat atgttaacgt ctaatttgac ttttacagtt   2580
tattctgatt tattatcttt cgtttctgca gacacggttg aacccattaa cgcagttgct   2640
tttgacaata tgcgcattat gaacgaactg taa                                2673
```

<210> SEQ ID NO 11
<211> LENGTH: 2328
<212> TYPE: DNA
<213> ORGANISM: Human Rotavirus

<400> SEQUENCE: 11

```
atggcttcac tcatttatag acagcttctc actaattcat attcagtaga tttacatgat     60
gaaatagagc aaattggatc agaaaaaact caaaatgtaa ctataaatcc gagtccattt    120
gcacagacta gatatgctcc agtcaattgg ggtcatggag agataaatga ttcgactaca    180
gtagaaccaa tgttagatgg tccttatcag ccaactacat ttactccacc taatgattat    240
tggatactta ttaattcaaa tacaaatgga gtagtatatg aaagtacaaa taatagtgac    300
ttttggactg cagtcgttgc tattgaaccg cacgttaacc cagtagatag acaatatacg    360
atatttggtg aaagtaagca atttaatgtg agtaacgatt caaataaatg gaagtttta    420 gaaatgttta gaagcagtag tcaaaatgaa ttttataata gacgtacatt aacttctgat    480
actagatttg taggaatatt gaaatatggt ggaagagtat ggacatttca tggtgaaaca    540
ccaagagcta ctactgacag ttcaagtact gcaaatttaa ataatatatc aattacaatt    600
cattcagaat tttacattat tccaaggtcc caagaatcta atgtaatga atatattaat     660 aatggtctgc caccaattca aaatactaga atgtagttc cattgccatt atcatctaga    720
tcgatacagt ataagagagc acaagttaat gaagacatta tagtttcaaa aacttcatta    780
tggaaagaaa tgcagtataa tagggatatt ataattagat ttaaatttgg taatagtatt    840
gtaaaaatgg gaggactagg ttataaatgg tctgaaatat catataaggc agcaaattat    900
caatataatt acttacgtga cggtgaacaa gtaaccgcac acaccacttg ttcagtaaat    960
ggagtgaaca attttagcta taatggaggg tttctaccca ctgattttgg tatttcaagg   1020
tatgaagtta ttaaagagaa ttcctatgta tatgtagact attgggatga ttcaaaagca   1080
tttagaaata tggtatatgt tagatcatta gcagctaatt tgaattcagt gaatgtaca    1140 ggtggaagtt ataattttag tataccagta ggtgcatggc cagtaatgaa tggtggcgct   1200 gttcgttgc atttgccgg agttacatta tccacgcaat ttactgattt tgtatcattg    1260
aattcactac gatttagatt tagtttgaca gttgatgaac cacctttctc aatattgaga   1320
acacgtacag tgaatttgta cggattacca gccgctaatc caaataatgg aaatgaatac   1380
tacgaaatat caggaaggtt ttcactcatt tatttagttc caactaatga tgattatcag   1440
actccaatta tgaattcagt gacagtaaga caagatttag agcgccaact tactgatttg   1500
```

-continued

```
cgagaagaat ttaactcatt gtcacaagaa atagctatgg cacaattgat tgatttagca   1560
ctgttgcctc tagatatgtt ttccatgttt tcaggaatta aaagtacaat tgatttaact   1620
aaatcaatgg cgactagtgt aatgaagaaa tttagaaaat caaaattagc tacatcaatt   1680
tcagaaatga ctaattcatt gtcagatgct gcttcatcag catcaagaaa cgtttctatt   1740
agatcgaatt tatctgcgat ctcaaattgg actaatgttt caaatgatgt gtcaaacgta   1800
actaattcat tgaacgatat ttcaacacaa acgtctacaa ttagtaagaa atttagatta   1860
aaagaaatga ttactcaaac tgaaggaatg agctttgacg acatttcagc agctgtacta   1920
aaaacaaaaa tagatatgtc tactcaaatt ggaaaaaata ctttacctga catagttaca   1980
gaggcatctg agaaatttat tccaaaacga tcatatcgaa tattaaagga tgatgaagta   2040
atggaaatta atactgaagg aaaattcttt gcatacaaaa ttaatacatt tgatgaagtg   2100
ccattcgatg taaataaatt cgctgaacta gtaacagatt ctccagttat atcagcgata   2160
atcgatttta agacattgaa aaatttaaat gataattatg gaatcactcg tacagaagcg   2220
ttaaatttaa ttaaatcgaa tccaaatatg ttgcgtaatt tcattaatca aaataatcca   2280
attataagga atagaattga acagttaata ctacaatgta aattgtga               2328
```

```
<210> SEQ ID NO 12
<211> LENGTH: 1194
<212> TYPE: DNA
<213> ORGANISM: Human Rotavirus

<400> SEQUENCE: 12
atggaggttc tgtactcact gtcaaaaact cttaaagatg ctagggacaa aattgttgaa     60
ggtacattat attctaatgt tagcgatctt attcagcaat tcaatcaaat gatagtaact    120
atgaatggaa atgattttca gactggagga attggtaatt tacctgttag aaattggact    180
ttcgattttg gtctattagg tacaacactt ttgaacttgg atgctaatta tgttgagaat    240
gcaagaacta taattgaata ttttattgac tttattgata atgtatgtat ggatgaaatg    300
gcaagagaat ctcaaagaaa tggagtagcg ccacaatctg aagcgttgag aaagttagcg    360
ggaattaaat ttaagagaat aaatttcgat aattcatcag aatacataga aaattggaac    420
ttacaaaata gaagacagcg caccggattt gtttttcata aacctaacat atttccatac    480
tcagcttcat ttactctaaa tagatctcaa ccaatgcatg ataatttaat gggaaccatg    540
tggcttaatg ctggatcaga aattcaagtg gctggatttg actactcatg cgccataaat    600
gcaccagcga acatacagca atttgaacat atcgtccagc ttaggcgcgc actgactaca    660
gctactataa ctttattacc tgatgcagag agatttagtt ttccaagagt aattaattca    720
gctgatggcg cgactacatg gttctttaat ccagttattc taagaccaaa caatgtagag    780
gtagaatttt tgttgaatgg acaaattatt aatacatatc aggctagatt tggtactatc    840
atcgcaagaa attttgatgc aattcgttta ttatttcagt tgatgcgtcc acctaatatg    900
acaccagctg ttaatgcact gtttccacaa gcacaacctt ttcagcacca tgcaacagtt    960
ggacttacat tacgtattga atctgcggtt tgtgaatcag tgcttgcgga cgcaaatgaa   1020
actctgttag caaatgtgac cgcggtgcgt caagaatatg ccataccagt tggaccggta   1080
tttccaccag gcatgaattg gactgaatta attactaact attcgccatc tagagaagat   1140
aacttgcaac gcgttttcac ggtagcttcc attagaagca tgttgattaa gtga         1194
```

METHOD FOR PREPARING RECOMBINANT ANTIGEN COMPLEX USING ROTAVIRUS NANOPARTICLE

RELATED APPLICATIONS

This application claims priority from foreign patent application 10-2010-0041095, filed Apr. 30, 2010 in the Republic of Korea.

TECHNICAL FIELD

The present disclosure relates to a method for preparing a recombinant antigen complex using a rotavirus nanoparticle. More particularly, it relates to a construct for expressing a rotavirus antigen complex, a host cell transformed with the expression construct, a vaccine composition including the rotavirus antigen complex, a virus-like particle (VLP) of rotavirus having the rotavirus antigen complex, and a vaccine composition including the virus-like particle.

BACKGROUND

Human rotavirus (HRV) is the most common cause of diarrhea among infants and young children. Worldwide, including Korea, nearly 95% of children have been infected with the virus at least once by the age of 5, and it is known to account for ~40% of about 125 million diarrhea patients occurring every year. Hence, rotavirus is a very important pathogen in public health (Patel et al. 2011. *Pediatr Infect Dis J* 30: S1-S5). The virus is non-enveloped and is surrounded by a three-layered icosahedral protein capsid 75 nm in diameter, consisting of an outer capsid, an inner capsid and a core protein. It is known as a dsRNA virus consisting of 11 segments. Each segment codes for one of 6 structural proteins (VP1, VP2, VP3, VP4, VP6 and VP7) and 6 nonstructural proteins (NSPs 1-6) (Estes and Cohen, 1989. Rotavirus gene structure and function. *Microbiol Rev* 53: 410-449). Rotavirus is classified into 7 groups, from A through G, depending on the antigenicity of VP6. Group A rotaviruses, which are the most common globally, may be subdivided into glycoprotein type (G type) by the immunogenic protein VP7 and protease-sensitive type (P type) by VP4. At present, 23 G types and 32 P types are reported. In human, 9 serotypes including G1-G4, G6, G8-G10 and G12 and 8 genotypes including P[3], P[4], P[6], P[8]-P[11] and P[14] cause infections. The serotypes are not cross-protective (Banyai et al. 2009. *Arch Virol* 154: 1823-1829; Matthijnssens et al., 2009. *Future Microbiol* 4: 1303-1316).

According to the Centers for Disease Control and Prevention (CDC) of the US, annual cost spent for the treatment of rotavirus-associated diarrhea amounts to 10 million dollars in the US only. In Korea, 70% of infants and young children hospitalized for acute enteritis are those who are infected by the virus. Accordingly, the World Health Organization (WHO) is striving to reduce occurrence of rotavirus in developing countries and to develop vaccines against rotavirus in developed countries to save medical cost (Parashar et al. 2003. *Emerg Infect Dis* 9:565-572).

Meanwhile, infection with human hepatitis A virus (HAV) is increasing recently in the western part of the US, the Middle East and some regions in Asia. The spread of hepatitis A is a global concern. Also in Korea, hepatitis A is rapidly increasing in recent years in teenagers and those who are in their twenties who lack immunity against the virus. The infection is commonest in ages between 5 and 14 years. It is reported that about 30% of patients are aged 15 or younger. According to a survey in the US from 1982 through 1993, the incidence of hepatitis A (47%) was more frequent than hepatitis B (37%), and serologic test revealed that about 33% of the US population had been infected with hepatitis A virus (Gust et al. 1992. Vaccine 10: S56-S8). Hepatitis A virus is an RNA virus belonging to the family Picornaviridae, around 27 nm in diameter. After an incubation period of 28 days on average, it can induce acute liver disease characterized by such clinical symptoms as fever, malaise, appetite loss, nausea, abdominal pain, dark urine, jaundice, etc. Like rotavirus, it is non-enveloped and contains a single-stranded 7.5-kb RNA packaged in an icosahedral protein shell 27 nm in diameter. It is known to have one long ORF (P1-3) (Totsuka et al. 1999. *Intervirology* 42: 63-68).

Hepatitis A is mainly spread by the fecal-oral route, like rotavirus, via contact with contaminated food or drinking water. About 11-22% of hepatitis A patients are hospitalized. When an adult patient is hospitalized, he/she will have to be away from work for about 27 days. When the disease outbreaks, a preventive therapy is required for 11 people who contacted with the patient on average. In the US, the direct and indirect costs spent for one hepatitis A patient is estimated at 1,817-2,459 dollars for an adult and 433-1,492 dollars for one who is aged 18 or younger (WHO. 2000. MMWR *Wkly Epidemiol Rec* 75: 38-44). In Korea, hepatitis A is increasing rapidly nationwide, centered around the metropolitan areas including Seoul, Incheon and Gyeonggi. According to an epidemiological study by the Korea Centers for Disease Control and Prevention, the outbreak of hepatitis A is increasing quickly, with 2,233 cases in 2007 and 1,575 cases between January and June of 2008 (KCDC, 2010).

Throughout the specification, a number of publications and patent documents are referred to and cited. The disclosure of the cited publications and patent documents is incorporated herein by reference in its entirety to more clearly describe the state of the related art and the present disclosure.

DETAILED DESCRIPTION OF THE INVENTION

The inventors of the present disclosure have made efforts to develop an expression vector system capable of expressing a recombinant rotavirus antigen complex loaded with a heterologous virus epitope and a method for producing a rotavirus-like particle including the recombinant rotavirus antigen complex using the same. As a result, the present inventors have developed a baculovirus expression vector system capable of expressing a hepatitis A virus epitope and a rotavirus antigen at the same time. They have transformed a host cell using the system, successfully expressed the virus antigen complex, and identified its immunogenicity. Furthermore, they have successfully produced a virus-like particle of rotavirus having the antigen complex by expressing the antigen complex together with an additional virus structural protein, and identified the immunogenicity of the virus-like particle.

The present disclosure is directed to providing a construct for expressing a rotavirus antigen complex comprising a heterologous virus antigen.

The present disclosure is also directed to providing a host cell transformed with the construct for expressing a rotavirus antigen complex.

The present disclosure is also directed to providing a vaccine composition comprising the rotavirus antigen complex.

The present disclosure is also directed to providing a method for producing the rotavirus antigen complex.

The present disclosure is also directed to providing a virus-like particle of rotavirus comprising an antigen complex protein of a hepatitis A virus antigen and a rotavirus antigen.

The present disclosure is also directed to providing a vaccine composition comprising the virus-like particle of rotavirus.

The present disclosure is also directed to providing a method for producing the vaccine composition comprising the virus-like particle of rotavirus.

The present disclosure is also directed to providing a method of vaccination comprising administering to a subject in need thereof an effective amount of a vaccine composition.

Other features and aspects will be apparent from the following detailed description, drawings, and claims.

In one general aspect, the present disclosure provides a construct for expressing a rotavirus antigen complex comprising: (i) a nucleotide sequence encoding an antigen complex in which a heterologous virus antigen and a rotavirus antigen are linked; and (ii) a promoter operatively linked to the sequence encoding the antigen complex.

As used herein, the term "antigen complex" refers to a chimeric antigen comprising two or more different antigens or epitopes at the same time.

One of the prominent technical features of the present disclosure is that it provides an expression construct system capable of expressing a rotavirus antigen complex loaded with a heterologous virus epitope wherein the heterologous virus epitope is linked to a rotavirus antigen.

As used herein, the term "expression construct" refers to an essential element for expression including a nucleotide sequence to be expressed and a sequence for inducing the expression of the sequence (e.g., a promoter). Specifically, the expression construct may include a transcription regulatory sequence, the nucleotide sequence to be expressed, and a polyadenylation sequence.

As used herein, the term "promoter" refers to a transcription regulatory sequence capable of inducing transcription of a target gene in a eukaryotic cell. Non-limiting examples of the promoter sequence operable in the eukaryotic cell include cytomegalovirus immediate early promoter, SV40 promoter (SV40 late promoter and SV40 early promoter), herpes simplex virus (HSV) tk promoter, adenovirus 2 major late promoter (PAdmI), adenovirus 2 early promoter (PAdE2), human parvovirus-associated virus (AAV) p19 promoter, Epstein-Barr virus (EBV) promoter, Rous sarcoma virus (RSV) promoter, Vaccinia virus 7.5K promoter, mouse metallothionein (MT) promoter, MMTV LTR promoter, HIV LTR promoter, β-actin promoter, EF1 alpha promoter, human IL-2 gene promoter, human IFN gene promoter, human IL-4 gene promoter, human lymphotoxin gene promoter, human GM-CSF gene promoter, and human hemoglobin-, human muscle creatine- or human metallothionein-derived promoter.

As used herein, the term "operatively linked" refers to a functional linkage between a nucleotide expression regulatory sequence (e.g., promoter, signal sequence, or array of transcription factor binding sites) and a nucleotide sequence, wherein the regulatory sequence directs transcription and/or translation of the nucleotide sequence.

The expression construct of the present disclosure may comprise a polyadenylation sequence as a transcriptional termination sequence, which includes, for example, bovine growth hormone terminator (Gimmi, E. R., et al., *Nucleic Acids Res.* 17: 6983-6998 (1989)), SV40-derived polyadenylation sequence (Schek, N, et al., *Mol. Cell Biol.* 12: 5386-5393 (1992)), HIV-1 polyA (Klasens, B. I. F., et al., *Nucleic Acids Res.* 26: 1870-1876 (1998)), β-globin polyA (Gil, A., et al, *Cell* 49: 399-406 (1987)), HSV TK polyA (Cole, C. N. and T. P. Stacy, *Mol. Cell. Biol.* 5: 2104-2113 (1985)), or polyomavirus polyA (Batt, D. B and G. G. Carmichael, *Mol. Cell. Biol.* 15: 4783-4790 (1995)), but is not limited thereto.

Furthermore, the expression construct of the present disclosure may comprise an antibiotic-resistant gene commonly employed in the art as a selection marker. For example, genes resistant to ampicillin, gentamicin, carbenicillin, chloramphenicol, streptomycin, kanamycin, geneticin (G418), neomycin or tetracycline may be included.

The recombinant antigen complex expression construct of the present disclosure may be prepared in various forms, including plasmid or viral vector systems. Specifically, the expression construct of the present disclosure may be a viral vector system, for example, vector systems of adenovirus, adeno-associated virus, retrovirus, lentivirus, Vaccinia virus, herpes simplex virus, baculovirus, etc., but is not limited thereto. Most specifically, the expression construct may be constructed as a baculovirus transfer vector.

According to a specific embodiment of the present disclosure, in the rotavirus antigen complex expression construct, the heterologous virus may be hepatitis A virus.

According to another specific embodiment of the present disclosure, the hepatitis A virus antigen may be domain 2 (D2) or domain 3 (D3). More specifically, D2 and D3 may respectively be a polypeptide having an amino acid sequence of SEQ ID NO: 2 and SEQ ID NO: 3.

According to another specific embodiment of the present disclosure, the rotavirus antigen may be VP7 protein. More specifically, the rotavirus antigen VP7 protein may be a polypeptide having an amino acid sequence of SEQ ID NO: 1.

According to another specific embodiment of the present disclosure, the hepatitis A virus antigen and the rotavirus antigen may be linked by a peptide linker.

According to another specific embodiment of the present disclosure, the peptide linker may be Leu-Glu-Pro-Gly or Lys-Asp-Glu-Leu. Lys-Asp-Glu-Leu promotes retention of the recombinant protein in the endoplasmic reticulum (ER) and, thus, improves antigen presenting effect by MHC class I.

According to a specific embodiment of the present disclosure, the construct for expressing a rotavirus antigen complex of the present disclosure comprises the DNA elements shown in FIG. 1.

In another general aspect, the present disclosure provides a host cell transformed with the construct for expressing a rotavirus antigen complex.

The host cell that is transformed with the rotavirus antigen complex expression construct of the present disclosure may be specifically an animal cell, more specifically a yeast cell, an insect cell or a mammalian cell, most specifically an insect cell. The insect cell may be, for example, *Spodoptera frugiperda* 21 (Sf21; Invitrogen), *Spodoptera frugiperda* 9 (Sf9; Invitrogen), *Trichoplusia ni* 5 (Tn5; Invitrogen), or the like, but is not limited thereto.

The animal cell may be transformed with the expression construct according to various methods known in the art. Non-limiting examples include microinjection (Capecchi, M. R., *Cell*, 22: 479 (1980)), calcium phosphate precipitation (Graham, F. L. et al., *Virology*, 52: 456 (1973)), electroporation (Neumann, E. et al., *EMBO J.*, 1: 841 (1982)), liposome-mediated transfection (Wong, T. K. et al., *Gene*, 10: 87 (1980)), DEAE-dextran method (Gopal, *Mol. Cell. Biol.*, 5: 1188-1190 (1985)), gene bombardment (Yang et al., *Proc. Natl. Acad. Sci.*, 87: 9568-9572 (1990)), lithium acetate-DMSO method (Hill et al., *Nucleic Acid Res.*, 19, 5791 (1991)), etc.

In another general aspect, the present disclosure provides a recombinant rotavirus antigen complex wherein the hepatitis A virus antigen and the rotavirus antigen are linked with each other.

In another general aspect, the present disclosure provides a vaccine composition comprising the recombinant rotavirus antigen complex as an active ingredient.

According to a specific embodiment of the present disclosure, the rotavirus antigen may be VP7 protein, and the hepatitis A virus epitope may be D2 or D3.

According to another specific embodiment of the present disclosure, the VP7 protein may be a polypeptide having an amino acid sequence of SEQ ID NO: 1.

According to another specific embodiment of the present disclosure, D2 and D3 may respectively be a polypeptide having an amino acid sequence of SEQ ID NO: 2 and SEQ ID NO: 3.

According to another specific embodiment of the present disclosure, the hepatitis A virus antigen and the rotavirus antigen may be linked by a peptide linker. More specifically, the peptide linker may be Leu-Glu-Pro-Gly or Lys-Asp-Glu-Leu.

As demonstrated by the following examples, the recombinant rotavirus antigen complex protein of the present disclosure has antibody-inducing ability not only for rotavirus but also for hepatitis A virus.

The vaccine composition of the present disclosure comprises: (a) a pharmaceutically effective amount of the recombinant rotavirus antigen complex protein comprising the hepatitis A virus antigen; and (b) a pharmaceutically acceptable carrier. The vaccine composition of the present disclosure may be used to prevent various diseases caused by infection with hepatitis A virus or rotavirus. As used herein, the term "pharmaceutically effective amount" refers to an amount sufficient to achieve a preventive effect for the disease.

The pharmaceutically acceptable carrier included in the vaccine composition of the present disclosure may be one commonly used in the art. Non-limiting examples may include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc. In addition, the composition of the present disclosure may further include a lubricant, a wetting agent, a sweetener, a flavor, an emulsifier, a suspending agent, a preservative, or the like.

The vaccine composition of the present disclosure may be administered parenterally. For example, it may be administered intravenously, intra-abdominally, intramuscularly, subcutaneously or topically.

An adequate dose of the vaccine composition of the present disclosure may vary depending on such factors as preparation method, administration method, age, body weight and sex of the patient, severity of symptoms, administration time, administration route, rate of excretion, and responsivity. A physician of ordinary skill in the art will easily determine and diagnose the administration dose effective for treatment.

The vaccine composition of the present disclosure may be prepared into unit-dose or multiple-dose preparations by those skilled in the art using a pharmaceutically acceptable carrier and/or excipient according to a method known in the art. The preparation may be in the form of a solution in an oil or aqueous medium, a suspension, an emulsion, an extract, a powder, a granule, a tablet, or a capsule. It may further include a dispersant or a stabilizer.

In another general aspect, the present disclosure provides a method for producing a rotavirus antigen complex having a hepatitis A virus antigen, comprising: (a) culturing a host cell transformed with a recombinant baculovirus for expressing a rotavirus antigen complex comprising: (i) a nucleotide sequence encoding an antigen complex in which a hepatitis A virus antigen and a rotavirus antigen are linked; and (ii) a promoter operatively linked to the sequence encoding the antigen complex; and (b) isolating and purifying a recombinant rotavirus antigen complex protein from the cultured cell.

The transformed host cell may be cultured according to a common animal cell culturing method known in the art.

For culturing of the transformed host cell, any natural or synthetic medium containing a carbon source, a nitrogen source, an inorganic salt, etc. that may be effectively used by the cell may be used. The carbon source may include: a carbohydrate such as glucose, fructose and sucrose; starch or starch hydrolysate; an organic acid such as acetic acid and propionic acid; an alcohol such as methanol, ethanol and propanol; or the like. The nitrogen source may include: ammonia; an ammonium salt of an inorganic acid or an organic acid such as ammonium chloride, ammonium sulfate, ammonium acetate and ammonium phosphate; peptone, meat extract, yeast extract, corn steep liquor, casein hydrolysate, soybean extract, soybean hydrolysate; various fermented cells and digested product thereof; or the like. The inorganic salt may include potassium dihydrogen phosphate, dipotassium hydrogen phosphate, magnesium phosphate, magnesium sulfate, sodium chloride, manganese sulfate, copper sulfate, calcium carbonate, or the like.

The medium may be any one commonly employed for culturing of an animal cell. For example, Eagle's minimum essential medium (Eagle's MEM; Eagle, H. *Science* 130: 432 (1959)), α-MEM (Stanner, C. P. et al., *Nat. New Biol.* 230: 52 (1971)), Iscove's MEM (Iscove, N. et al., *J. Exp. Med.* 147: 923 (1978)), Medium 199 (Morgan et al., *Proc. Soc. Exp. Bio. Med.*, 73: 1 (1950)), CMRL 1066 and RPMI 1640 (Moore et al., *J. Amer. Med. Assoc.* 199: 519 (1967)), F12 (Ham, *Proc. Natl. Acad. Sci. USA* 53: 288 (1965)), F10 (Ham, R. G. *Exp. Cell Res.* 29: 515 (1963)), Dulbecco's modified Eagle's medium (DMEM; Dulbecco, R. et al., *Virology* 8: 396 (1959)), DMEM/F12 mixture (Barnes, D. et al., *Anal. Biochem.* 102: 255 (1980)), Waymouth's MB752/1 (Waymouth, C. J. *Natl. Cancer Inst.* 22: 1003 (1959)), McCoy's 5A (McCoy, T. A., et al., *Proc. Soc. Exp. Biol. Med.* 100: 115 (1959)), MCDB series (Ham, R. G. et al., *In Vitro* 14: 11 (1978)), or the like may be used. Detailed description about these media can be found in R. Ian Freshney, Culture of Animal Cells, A Manual of Basic Technique, Alan R. Liss, Inc., New York, which is incorporated herein by reference.

The culturing is carried out under aerobic conditions, for example, by shaking or spinning. Specifically, the culturing temperature is in the range from 15 to 40° C., and the culturing time is usually from 5 hours to 7 days. The pH of the medium may be adjusted to 3.0-9.0. The pH of the medium may be adjusted by adding, for example, an inorganic or organic acid, an alkaline solution, urea, calcium carbonate, ammonia, etc. If necessary, an antibiotic such as ampicillin and tetracycline may be added.

From the cultured transformed cell, the expressed antigen complex protein may be isolated and purified according to a method commonly employed in the art. Various methods including solubility-based fractionation using ammonium sulfate or PEG, ultrafiltration based on molecular weight, various chromatographic techniques (based on size, charge, hydrophobicity or affinity), or the like may be employed.

Usually, a combination of the above-mentioned methods is used for the isolation and purification.

In another general aspect, the present disclosure provides a virus-like particle of rotavirus comprising: (a) a polypeptide VP2, VP4 and VP6 of rotavirus; and (b) a fusion protein of a heterologous virus epitope and a rotavirus antigen VP7.

According to a specific embodiment of the present disclosure, the heterologous virus is hepatitis A virus.

According to another specific embodiment of the present disclosure, the fusion protein is a fusion protein D2-VP7 of a hepatitis A virus antigen D2 and a rotavirus antigen VP7.

According to a specific embodiment of the present disclosure, the polypeptide VP2 has an amino acid sequence of SEQ ID NO: 4, the polypeptide VP4 has an amino acid sequence of SEQ ID NO: 5, the polypeptide VP6 has an amino acid sequence of SEQ ID NO: 6, the polypeptide D2 has an amino acid sequence of SEQ ID NO: 2, and the polypeptide VP7 has an amino acid sequence of SEQ ID NO: 1.

According to another specific embodiment of the present disclosure, the fusion protein D2-VP7 is one in which D2 and VP7 are linked by a peptide linker Leu-Glu-Pro-Gly or Lys-Asp-Glu-Leu.

In another general aspect, the present disclosure provides a vaccine composition comprising a virus-like particle of rotavirus having (i) polypeptides of VP2, VP4 and VP6 of rotavirus; and (b) a fusion protein D2-VP7 of a hepatitis A virus antigen D2 and a rotavirus antigen VP7.

Description about the vaccine composition comprising the virus-like particle of rotavirus will be omitted since it is the same as that given with respect to the rotavirus antigen complex.

In another general aspect, the present disclosure provides a method for producing a virus-like particle of rotavirus having a hepatitis A virus antigen, comprising: (a) culturing a host cell transformed with four recombinant baculoviruses of (i) a first recombinant baculovirus comprising a VP2 encoding nucleotide sequence operatively linked to a promoter; (ii) a second recombinant baculovirus comprising a VP4 encoding nucleotide sequence operatively linked to a promoter; (iii) a third recombinant baculovirus comprising a VP6 encoding nucleotide sequence operatively linked to a promoter; and (iv) a fourth recombinant baculovirus comprising a fusion protein D2-VP7 encoding nucleotide sequence operatively linked to a promoter; and (b) isolating and purifying a virus-like particle of rotavirus from the cultured cell.

According to a specific embodiment of the present disclosure, the polypeptide VP2 has an amino acid sequence of SEQ ID NO: 4, the polypeptide VP4 has an amino acid sequence of SEQ ID NO: 5, the polypeptide VP6 has an amino acid sequence of SEQ ID NO: 6, the polypeptide D2 has an amino acid sequence of SEQ ID NO: 2, and the polypeptide VP7 has an amino acid sequence of SEQ ID NO: 1. According to another specific embodiment of the present disclosure, the fusion protein D2-VP7 is one in which D2 and VP7 are linked by a peptide linker Leu-Glu-Pro-Gly or Lys-Asp-Glu-Leu.

Description about the method for producing the virus-like particle of rotavirus will be omitted since it is the same as that given with respect to the rotavirus antigen complex protein.

In another general aspect, the present disclosure provides a method of vaccination comprising administering to a subject in need thereof an effective amount of a vaccine composition which comprises a recombinant rotavirus antigen complex wherein a hepatitis A virus antigen is linked with a rotavirus antigen.

In another general aspect, the present disclosure provides a method of vaccination comprising administering to a subject in need thereof an effective amount of a vaccine composition which comprises a virus-like particle of rotavirus having (i) polypeptides of VP2, VP4 and VP6 of rotavirus; and (ii) a fusion protein D2-VP7 of a hepatitis A virus antigen D2 and a rotavirus antigen VP7.

BRIEF DESCRIPTION OF THE DRAWINGS

The file of this patent or application publication contains at least one drawing executed in color. Copies of this patent or application publication with color drawing(s) will be provided by the Office upon request and payment of the necessary fee.

FIG. 2a shows a result of total protein analysis by SDS-PAGE (lane 1: uninfected, lane 2: D2-VP7 antigen complex, lane 3: D3-VP7 antigen complex).

FIG. 2b shows a Western blot analysis result using anti-V5 antibody (lane N: uninfected, lane 1: D2-VP7 antigen complex, lane 2: D3-VP7 antigen complex).

FIG. 4a shows a measurement result using anti-rotavirus rabbit serum comprising an antibody specific for rotavirus Wa (lane 1: uninfected Sf9 cell, lane 2: D2-VP7 antigen complex, lane 3: D3-VP7 antigen complex).

FIG. 4b shows a measurement result using hepatitis A virus-infected patient serum comprising an antibody specific for hepatitis A virus (lane 1: uninfected Sf9 cell, lane 2: D2-VP7 antigen complex).

FIG. 5a and FIG. 5b show an immunogenicity evaluation result of a recombinant antigen complex protein D2-VP7 by ELISA. The recombinant antigen complex protein D2-VP7 was injected to a rabbit for immunization, and serum isolated therefrom was subjected to antibody measurement.

FIG. 5a shows an antibody measurement result of the rabbit serum immunized with the rotavirus Wa antigen. [ ◆ : negative rabbit serum as negative control, ■ : rabbit serum immunized with rotavirus Wa as positive control, ▲ : rabbit serum immunized with the recombinant antigen complex protein D2-VP7] Absorbance (OD value) is shown on the ordinate and dilution rate is shown on the abscissa.

FIG. 5b shows an antibody measurement result of the rabbit serum immunized with the hepatitis A virus HM175 antigen. [ ◆ : negative rabbit serum as negative control, ■ : rabbit serum immunized with hepatitis A virus HM175 antigen as positive control, ▲ : rabbit serum immunized with the recombinant antigen complex protein D2-VP7] Absorbance (OD value) is shown on the ordinate and dilution rate is shown on the abscissa.

In FIG. 6a, panel A shows a result of measuring reactivity between an MA104 cell infected with rotavirus Wa and an unimmunized normal rabbit serum, and panel B shows a result of measuring reactivity between an MA104 cell infected with rotavirus Wa and a rabbit serum immunized with the recombinant antigen complex protein D2-VP7.

In FIG. 6b, panel A shows a result of measuring reactivity between an FRhK-4 cell infected with hepatitis A virus HM175 and an unimmunized normal rabbit serum, and panel B shows a result of measuring reactivity between an FRhK-4 cell infected with hepatitis A virus HM175 and a rabbit serum immunized with the recombinant antigen complex protein D2-VP7.

In FIG. 7a, panel A shows an MA104 cell infected with rotavirus Wa (positive control), panel B shows a result of adding a normal rabbit serum to an MA104 cell infected with rotavirus Wa (negative control), and panel C shows a result of adding a rabbit antiserum (X 320) against a recombinant antigen complex protein D2-VP7 to an MA104 cell infected with rotavirus Wa.

In FIG. 7b, panel A shows an FRhK-4 cell infected with hepatitis A virus HM175 (positive control), panel B shows a result of adding a normal rabbit serum to an FRhK-4 cell infected with hepatitis A virus HM175 (negative control), and panel C shows a result of adding a rabbit antiserum (X 160) against a recombinant antigen complex protein D2-VP7 to an FRhK-4 cell infected with hepatitis A virus HM175.

FIG. 10a shows an antibody measurement result of the mouse serum immunized with the rotavirus VLP for the rotavirus Wa antigen. [ –◆– : negative mouse serum as negative control, –■– : mouse serum immunized with rotavirus Wa as positive control, –▲– : mouse serum immunized with the rotavirus VLP). Absorbance (OD value) is shown on the ordinate and dilution rate is shown on the abscissa].

FIG. 10b shows an antibody measurement result of the mouse serum immunized with the hepatitis A virus HM175 antigen. [ –◆– : negative mouse serum as negative control, –■– : mouse serum immunized with hepatitis A virus HM175 antigen as positive control, –▲– : mouse serum immunized with the rotavirus VLP]. Absorbance (OD value) is shown on the ordinate and dilution rate is shown on the abscissa.

Figure 1:
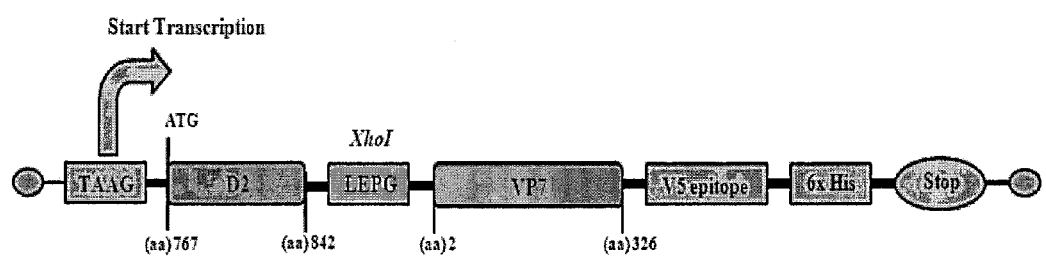
FIG. 1 shows baculovirus expression vector systems developed by the inventors of the present invention which express a recombinant antigen complex comprising a hepatitis A virus antigen and a rotavirus antigen.
Figure 1:
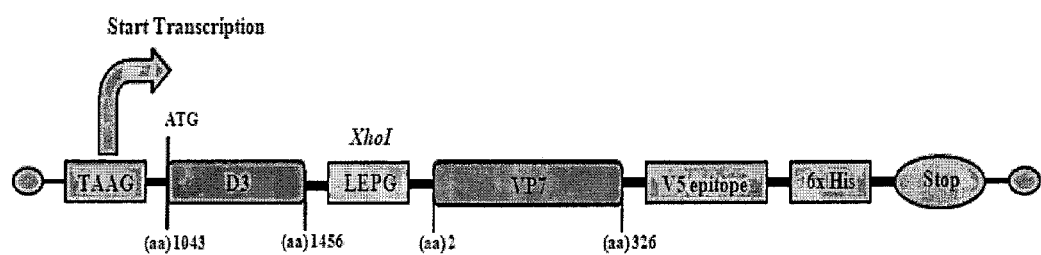

The examples and experiments will now be described. The following examples and experiments are for illustrative purposes only and not intended to limit the scope of this disclosure.

EXAMPLES

Methods and Materials

1. Materials

Insect Sf9 (*Spodoptera frugiperda*) cells were acquired from the Korean Cell Line Bank (KCLB; Korea) and used for preparation of recombinant baculovirus. Sf9 cells were cultured in TNM-FH medium containing 10% fetal bovine serum (FBS) at 90 rpm and 27° C. using a 250-mL spinner flask. Number of cells and cell viability were measured using a hemocytometer according to the trypan blue exclusion method. Epitope genes were acquired from serotype G1P[8] Wa rotavirus and HM175 hepatitis A virus genomes, and the Bac-N-Blue baculovirus expression vector system (Invitrogen) was used for preparation of recombinant baculovirus.

2. Reagents and Test Animals

Restriction enzyme XhoI and T4 DNA ligase were purchased from New England Biolabs. The baculovirus transfer vector pBlueBac4.5/V5-His and the baculovirus expression system Bac-N-Blue™ were purchased from Invitrogen. The Plasmid Miniprep kit was purchased from Bioneer. An antiserum isolated from a human patient infected with hepatitis A virus and an antiserum from a rabbit infected with Wa rotavirus were used for analysis of immunogenicity. 6-8 week-old SPF female New Zealand white rabbits were used as test animal. They were accustomed for 2 weeks before test.

3. Construction of Recombinant Baculovirus Expression System for Expression of Antigen Complex Having Rotavirus and Hepatitis a Virus Epitopes VP7 gene of rotavirus (HRV) capsid was synthesized from a cDNA obtained from Wa (G1P[8]) rotavirus RNA by RT-PCR. Hepatitis A virus (HAV) domain 2 (D2, amino acids 767-842) and domain 3 (D3, amino acids 1403-1456) genes were synthesized from a cDNA obtained from HM175 hepatitis A virus RNA by RT-PCR. By artificially inserting an XhoI restriction enzyme site to a primer, DNA fragments encoding two kinds of recombinant antigen complexes comprising hepatitis A virus and rotavirus epitopes were obtained: (1) HAV D2 and HRV VP7 (D2-VP7), (2) HAV D3 and HRV VP7 (D3-VP7). The recombinant genes were amplified by PCR and cloned into the baculovirus transfer vector pBlueBac4.5 (Invitrogen) to prepare a recombinant baculovirus transfer vector. The prepared recombinant transfer vector was subjected to base sequencing analysis to ensure that the cloning was performed accurately. The prepared recombinant baculovirus transfer vector was mixed with Bac-N-Blue™ linearized baculovirus DNA and Cellfectin® II that had been prepared in serum-free medium, and reacted at room temperature for 15 minutes. Then, insect Sf9 cells ($2\times10^6$ cells/5 mL, 60-mm plates) were added. The mixture solution was replaced with TNM-FH medium containing 10% FBS, and the recombinant baculovirus was identified by the standard plaque assay.

4. Identification of Expressed Protein by SDS-PAGE and Western Blot

Recombinant antigen complex protein expression sample was isolated by 10% SDS-PAGE and identified by Coomassie Brilliant Blue R-250 (Bio-Rad) staining. In order to identify the presence of the expressed protein, all the protein components were transferred to an Immuno-Blot™ PVDF membrane (Bio-Rad), and the membrane was blocked using 5% skim milk. As primary antibody, the rotavirus Wa rabbit antiserum and the hepatitis A patient antiserum were prepared in a mixture of Tris-buffered saline and Tween 20 (TBS-T; 20 mM Tris-HCl, 500 mM NaCl, 0.1% Tween 20, pH 7.9). After reaction with the prepared primary antibody for 1 hour, reaction was further carried out using peroxidase-conjugated goat anti-rabbit IgG (1:2000 dilution in TBS-T, Invitrogen) as secondary antibody. The expressed protein was identified by electrochemiluminescence (ECL) after exposure on an X-ray film (Kodak).

5. Immunization of Rabbit

50 μg of the recombinant antigen complex protein D2-VP7 was intramuscularly injected to two New Zealand white rabbits together with Freund's complete adjuvant (day 0). On day 28, boosting was performed by injecting Freund's incomplete adjuvant. On day 40, blood was taken from the ear vein, serum was isolated therefrom, and the formation of antibody was identified by ELISA.

6. Detection of Specific Antibody by ELISA

The isolated and purified rotavirus Wa antigen and hepatitis A virus HM175 antigen (Abcam, UK) were prepared in a coating solution (0.1 M $Na_2CO_3$, 0.1 M $NaHCO_3$, pH 9.4) at a concentration of 0.1 μg per well, and coated on a 96-well immunoplate overnight at 4° C. The plate was washed 3 times with 200 μL of PBS-T (1×PBS with 0.05% Tween 20), and then blocked using 5% (w/v) skim milk. The immunized serum obtained from the rabbit was serially diluted and reacted at 37° C. or 1 hour. After washing, 100 μL of peroxidase-conjugated goat anti-rabbit IgG (diluted in PBS-T, containing 5% skim milk) was added into each well, and reaction was performed at 37° C. for 1 hour. After adding orthophenylenediamine (OPD) as substrate and reacting for 5 minutes, 50 μL of 1 M $H_2SO_4$ was added to each well to stop the reaction. Then, antibody was quantitated by measuring absorbance at 492 nm using an ELISA reader (NanoQuant).

7. Identification of Antibody Specificity Through Virus-Antibody Reaction 7-1. Antibody Specificity for Rotavirus To MA104 cells cultured on a 96-well glass plate (Nunc), 100 μL of 10× diluted Wa rotavirus solution and 100 μL of a viral medium (Eagle's medium containing 0.5% of 1 mg/mL trypsin) were added and reaction was performed until a cytopathic effect was observed. After removing the culture medium and adding 80% acetone and incubating for 10 minutes to immobilize the cells, the cells were washed 3 times with PBS (pH 7.2). Then, after adding 100 μL of the recombinant antigen complex protein D2-VP7 immunized serum obtained from the rabbit as primary antibody, which had been diluted 50× with PBS, reaction was performed at 37° C. for 1 hour. After washing 3 times with PBS, 50 μL of 50× diluted FITC-conjugated goat anti-rabbit IgG (Invitrogen) was added as secondary antibody. Then, after reacting at 37° C. for 1 hour followed by further washing 3 times with PBS, 80% glycerol (Sigma) was added to terminate the reaction. Then, it was observed under a confocal microscope (Carl Zeiss) whether the antibody obtained from the rabbit exhibits specificity for rotavirus.

7-2. Antibody Specificity for Hepatitis A Virus

To FRhk-4 cells cultured on a 96-well glass plate (Nunc), 100 μL of 10× diluted HM175 hepatitis A virus solution and 100 μL of a viral medium (Eagle's medium containing 2% bovine serum) were added and reaction was performed until a cytopathic effect was observed. After removing the culture medium and adding 80% acetone and reacting for 10 minutes to immobilize the cells, the cells were washed 3 times with PBS (pH 7.2). Then, after adding 100 μL of the recombinant antigen complex protein D2/VP7 immunized serum obtained from the rabbit as primary antibody, which had been diluted 50× with PBS, reaction was performed at 37° C. for 1 hour. After washing 3 times with PBS, 50 μL of fiftyfold diluted FITC-conjugated goat anti-rabbit IgG (Invitrogen) was added as secondary antibody. Then, after reacting at 37° C. for 1 hour followed by further washing 3 times with PBS, 80% glycerol (Sigma) was added to terminate the reaction. Then, it was observed under a confocal microscope (Carl Zeiss) whether the antibody obtained from the rabbit exhibits specificity for hepatitis A virus.

8. Formation of Neutralizing Antibody

After deactivation of complement by incubating the recombinant antigen complex protein D2-VP7 immunized serum obtained from the rabbit at 56° C. for 30 minutes, the titer of the Wa rotavirus and HM175 hepatitis A virus solutions was measured by $TCID_{50}$. After adding 50 μL of each virus containing 100 doses $TCID_{50}/25$ μL (diluted in Eagle's medium at 1:10 for HAV and 1:640 for rotavirus) to a 96-well plate, 50 μL of the serum obtained from the rabbit, which had been diluted tenfold, was serially diluted two-fold and added to each well. After uniformly mixing, the mixture was incubated at 37° C. for 1 hour. After adding 50 μL of each virus-immunized serum mixture to the cell culture plate and then adding 50 μL of maintenance medium (Eagle's medium containing 2% bovine serum for HAV, and Eagle's medium containing 1 mg/mL trypsin for rotavirus), incubation was performed for 5 days. Then, formation of the neutralizing antibody from the immunized serum was identified by measuring the degree of denaturation of the cells using an inverted microscope (Leica) according to the ACTG Laboratory Technologist Committee's manual (revised version 1.0, May 25, 2004).

$$M=xk+d[0.5-(1/n)(r)] \qquad \text{Spearman-Karber formula}$$

xk=dose of the highest dilution
r=sum of the number of "−" responses
d=spacing between dilutions
n=wells per dilution 9. Synthesis of Virus-Like Particle of Rotavirus 9-1. Infection of Cells Sf9 cells cultured in 250 mL of TNM-FH medium containing 10% FBS and 0.1% Pluronic F-68 to about $3 \times 10^6$ cells/mL concentration were concentrated centrifugally and infected simultaneously with 4 recombinant baculoviruses comprising polynucleotides encoding VP2, VP4, VP6 and D2-VP7 with an MOI of 5 pfu/cell. After adsorbing the viruses for about 3-4 hour in a centrifugal tube, the infected cell solution was centrifuged and the supernatant was replaced with a fresh medium. The medium was 220 mL of Grace's insect medium containing 10% FBS and 0.1% Pluronic F-68. Then, the cells were cultured at 27° C. for 5-7 days.

9-2. Isolation and Purification of Virus-Like Particle of Rotavirus

The infected cell culture was ultracentrifuged at 12,000 rpm for 30 minutes.

To the supernatant containing the virus-like particle (VLP), 1.5 mL of 35% sucrose cushion (sucrose in TNC buffer, 10 mM Tris-HCl, pH 7.5, 140 mM NaCl, 10 mM $CaCl_2$) was added. Then, by centrifuging at 25,000 rpm for 90 minutes using an SW28 rotor (Beckman Coulter), the VLP was obtained as precipitate. The obtained VLP precipitate was suspended in 4 mL of TNC buffer and, after adding 0.42 g CsCl/mL, centrifuged at 35,000 rpm for 18 hours using an SW50.1 rotor (Beckman Coulter). Following the centrifugation, two identified bands, i.e. the bottom band (VLP) and the top band (CLP), were recovered using a disposable syringe, suspended respectively in 6 mL of TNC buffer, and then centrifuged at 35,000 rpm for 120 minutes using an SW41 rotor (Beckman Coulter). The VLP pellet was suspended in TNC buffer and identified by electron microscopic analysis.

9-3. Immunization

50 μg of each of the purified bottom band (VLP) and top band (CLP) was subcutaneously injected to two mice (Balb/c) together with Freund's complete adjuvant at 2-3 sites on the back. 14, 35 and 56 days later, boosting was performed by injecting Freund's incomplete adjuvant. 60 days later, blood was taken from the vein, serum was isolated therefrom, and formation of antibody was identified by ELISA.

Result

1. Construction of Recombinant Baculovirus Expression System for Expressing of Antigen Complex Having Rotavirus and Hepatitis A Virus Epitopes FIG. 1 schematically shows baculovirus expression vector systems developed by the inventors of the present disclosure which express a recombinant antigen complex comprising a hepatitis A virus antigen and a rotavirus antigen. As shown in FIG. 1, expression systems for two kinds of recombinant antigen complex of rotavirus and hepatitis A virus antigens, which are named D2-VP7 and D3-VP7 respectively, have been fabricated. 1,215-bp and 1,149-bp recombinant antigen protein amplification products were obtained by overlap extension PCR, and they were respectively inserted to the baculovirus transfer vector pBlueBac4.5 (Invitrogen). Thus prepared recombinant baculovirus transfer vectors were subjected to DNA base sequence analysis. It was identified that the cloned base sequence was fused in frame.

2. Expression of Recombinant Antigen Complex Protein in Insect Sf9 Cells

Figure 2A:
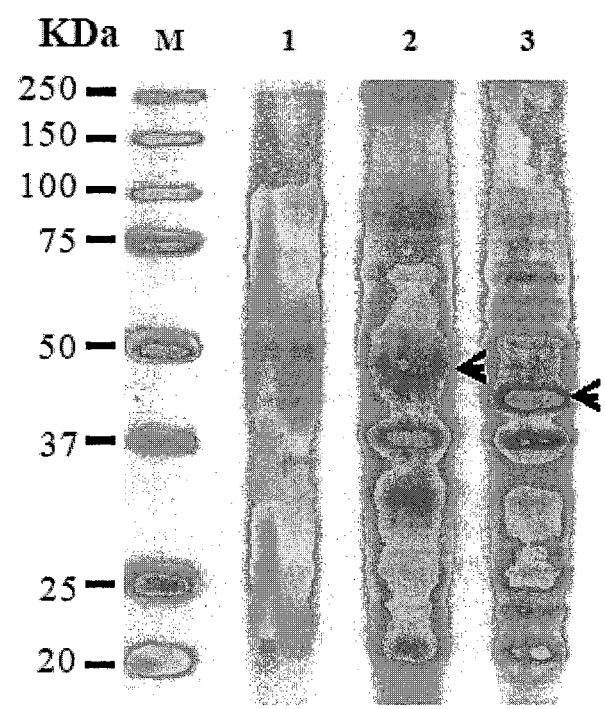
FIG. 2a and FIG. 2b show that a recombinant antigen complex protein is expressed normally in an insect Sf9 cell infected with the recombinant baculovirus vector of the present invention.
Figure 2B:
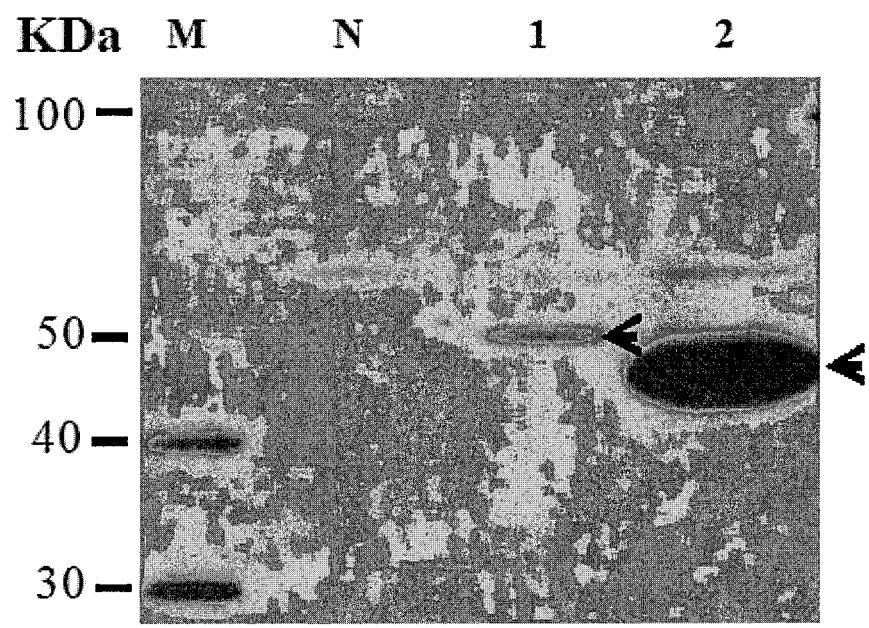
Figure 3:
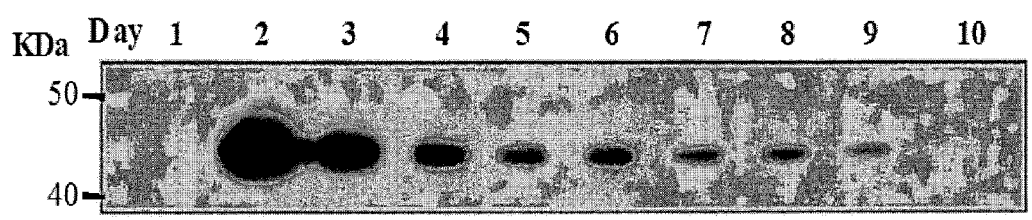
FIG. 3 shows expression of a recombinant antigen complex protein D2-VP7 of the present invention in an insect Sf9 cell (lane 1: uninfected Sf9 cell, lanes 1-10: 1-10 days after viral infection).

An insect Sf9 (*Spodoptera frugiperda* 9) cell was introduced into the recombinant baculovirus expression vectors and expression was identified through whole cell protein analysis. It was identified that the expected two recombinant antigen complex protein products were expressed in the insect cell (FIG. 2a). In particular, specific protein products corresponding to their size could be identified by using V5 antibody (FIG. 2b). This result suggests that the recombinant antigen complex proteins are stably expressed by the recombinant antigen complex protein expression systems of the present disclosure comprising the rotavirus antigen and the hepatitis A virus antigen at the same time. In order to investigate the change in expression of the recombinant antigen complex protein in the insect Sf9 cell with time, the cell was infected with the recombinant baculovirus expressing D2-VP7 at 5 pfu/cell and observed for 10 days. The expression level was highest on day 2 after the infection. Then, the expression level was decreased gradually and reached the minimum on day 10 (FIG. 3). This indicates that, after the infection with the recombinant baculovirus, the cell was normally lysed in 10 days.

3. Immunogenicity of Recombinant Antigen Complex Protein

Figure 4A:
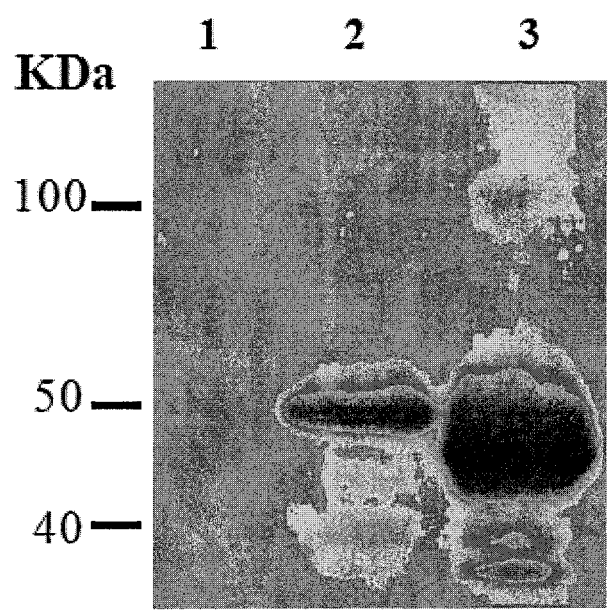
FIG. 4a and FIG. 4b show Western blot analysis result showing that a recombinant antigen complex protein of the present invention is recognized by antibodies specific for hepatitis A virus and rotavirus.
Figure 4B:
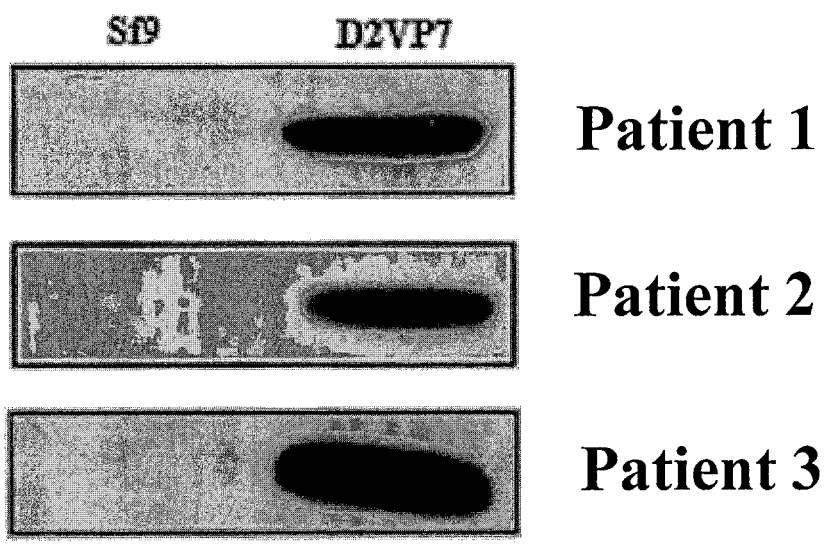

It was investigated whether the two recombinant antigen complex proteins comprising the rotavirus and hepatitis A virus antigens have immunogenicity. First, Western blot was carried out for the two recombinant antigen complex proteins using HAV antiserum from a human patient and rabbit antibody (IgG) against HRV Wa. As seen from FIG. 4a, both the expressed recombinant antigen complex proteins (D2-VP7 and D3-VP7) showed positive response to the rotavirus-specific antibody. In contrast, for the HAV antiserum acquired from three human patients, only the D2-VP7 showed a positive result (Table 1). As seen from FIG. 4b, it was identified that the recombinant antigen complex D2-VP7 is recognized by the HAV antiserum acquired from the three human patients.

TABLE 1

| Antibodies | Recombinant antigen complex protein | |
|---|---|---|
|  | D2-VP7 | D3-VP7 |
| Rabbit IgG against HRV Wa | (+) | (+) |
| HAV antiserum from human patient 1 | (+) | (−) |
| HAV antiserum from human patient 2 | (+) | (−) |
| HAV antiserum from human patient 3 | (+) | (−) |

This result shows that, among the two recombinant antigen complex proteins, D2-VP7 has immunogenicity against both rotavirus and hepatitis A virus.

Figure 5A:
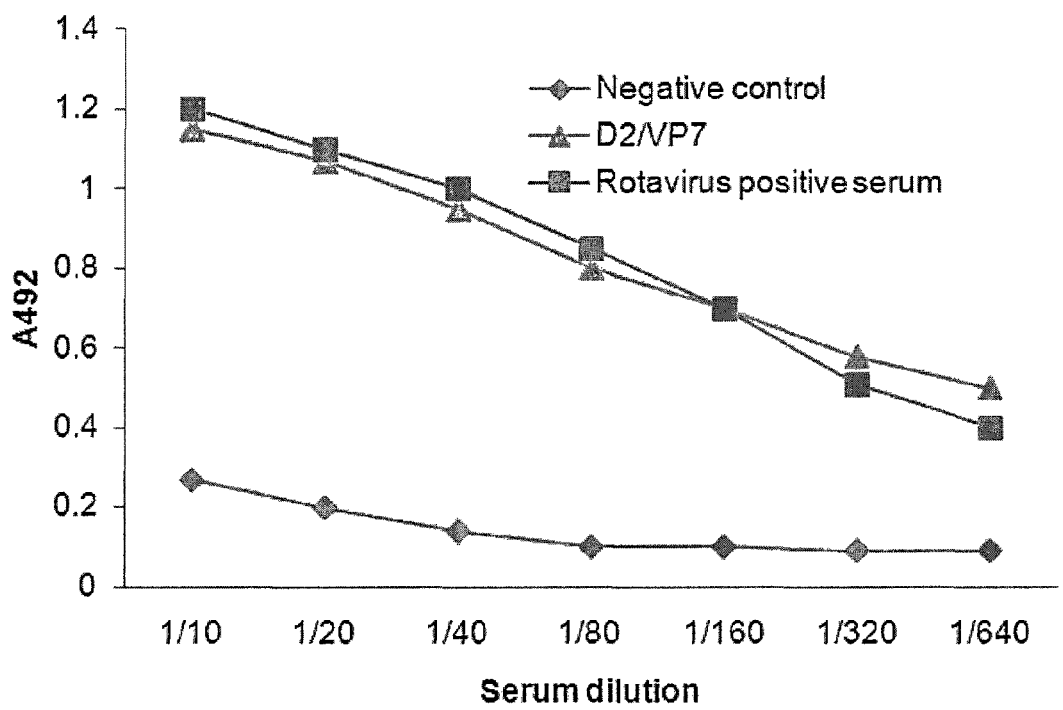
Figure 5B:
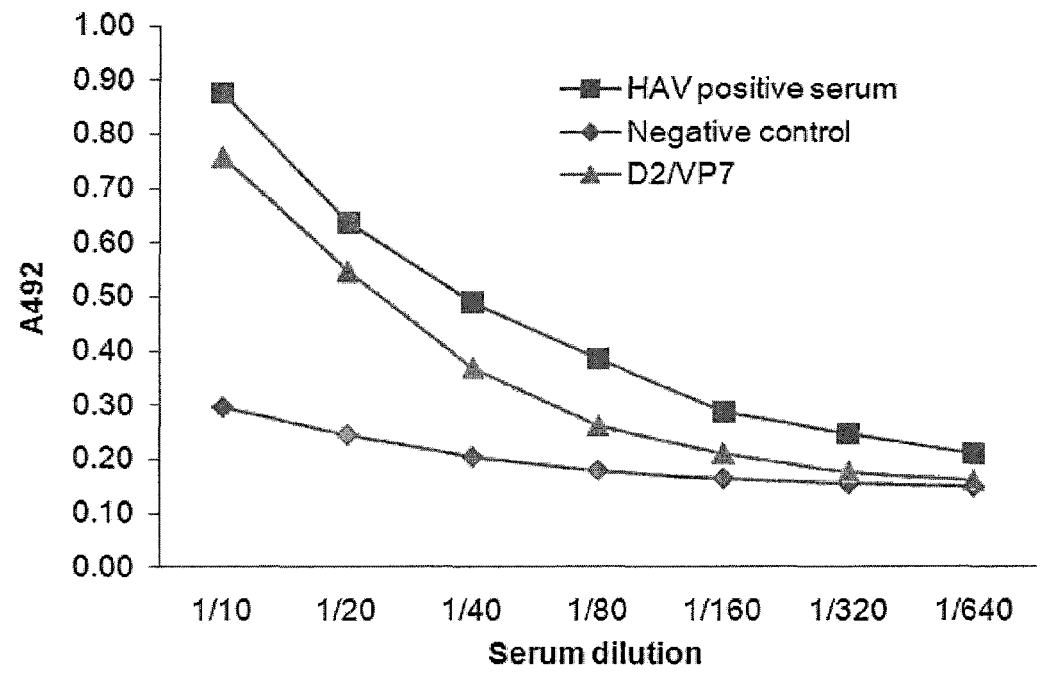

In order to further identify the immunogenicity of the recombinant antigen complex protein D2-VP7, the corresponding antigen was inoculated to a rabbit and it was investigated whether an antibody specific for the antigen is produced. As seen from FIG. 5a and FIG. 5b, the recombinant antigen complex protein D2-VP7 induced the production of the antibody specific for the rotavirus Wa and hepatitis A virus antigens.

Figure 6A:
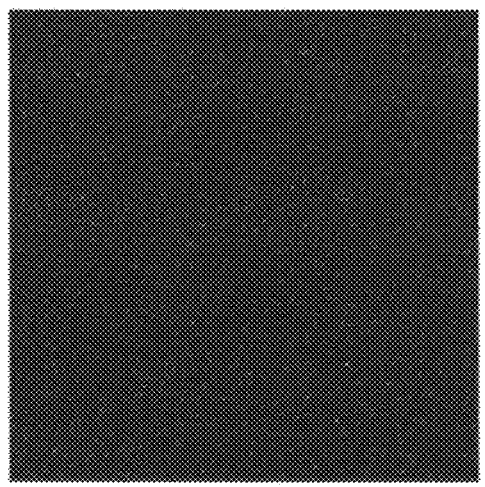
FIG. 6a and FIG. 6b show a result of measuring reactivity between an immunized serum obtained by inoculating a recombinant antigen complex protein D2-VP7 to a rabbit and virus using a confocal microscope.
Figure 6A:
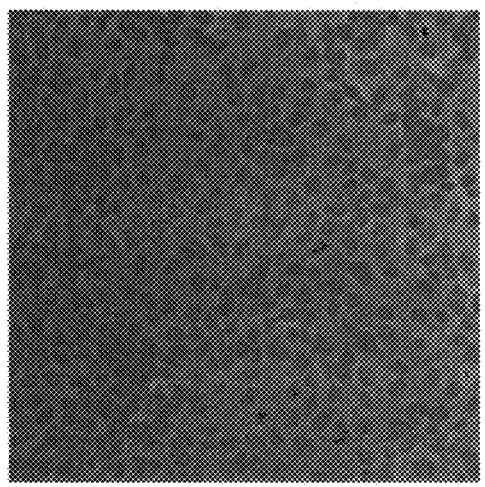
Figure 6B:
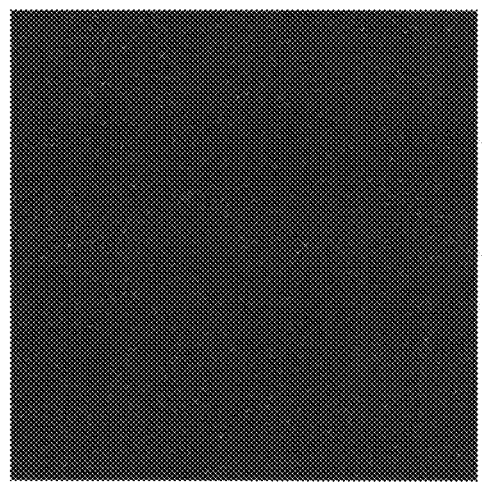
Figure 6B:
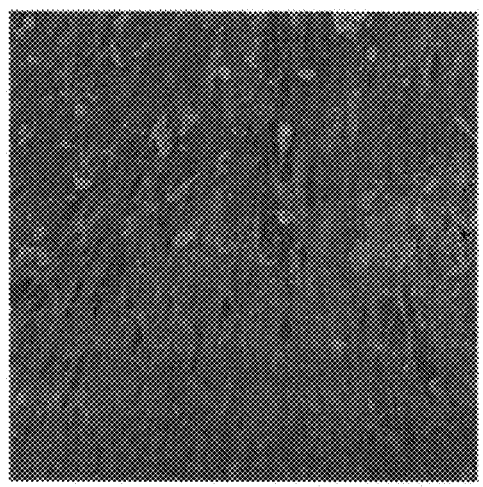

Furthermore, in order to identify whether the antibody specific for the recombinant antigen complex D2-VP7 reacts specifically with rotavirus and hepatitis A virus, the cultured cells infected with each virus were reacted with the serum immunized by inoculating the recombinant antigen complex D2-VP7. As seen from FIG. 6a and FIG. 6b, the immunized rabbit serum obtained by inoculating the recombinant antigen complex D2-VP7 reacted specifically with each virus. This result proves that the recombinant antigen complex D2-VP7 induces the production of the antibody specific for hepatitis A virus and rotavirus.

Figure 7A:
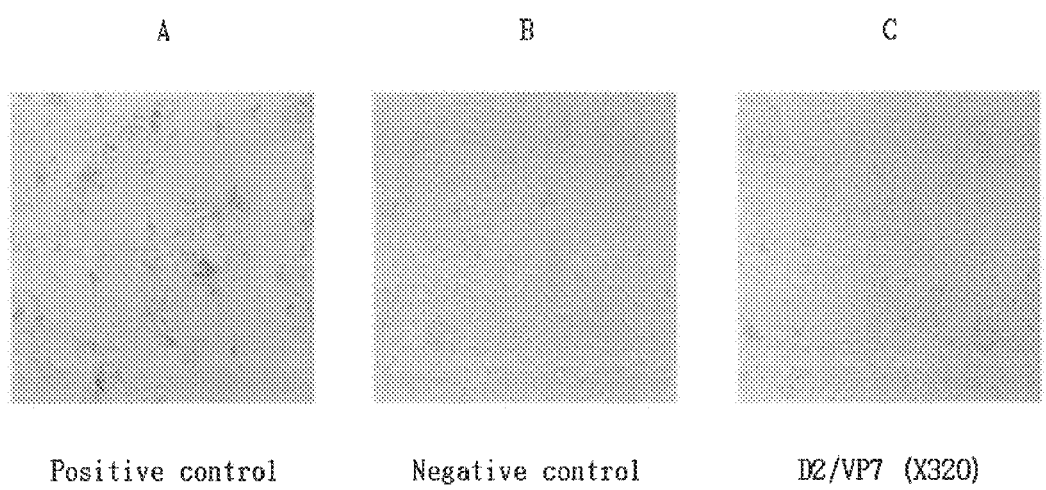
FIG. 7a and FIG. 7b show that neutralizing antibodies against rotavirus and hepatitis A virus are formed in a serum obtained by inoculating a recombinant antigen complex protein D2-VP7 to a rabbit.
Figure 7B:
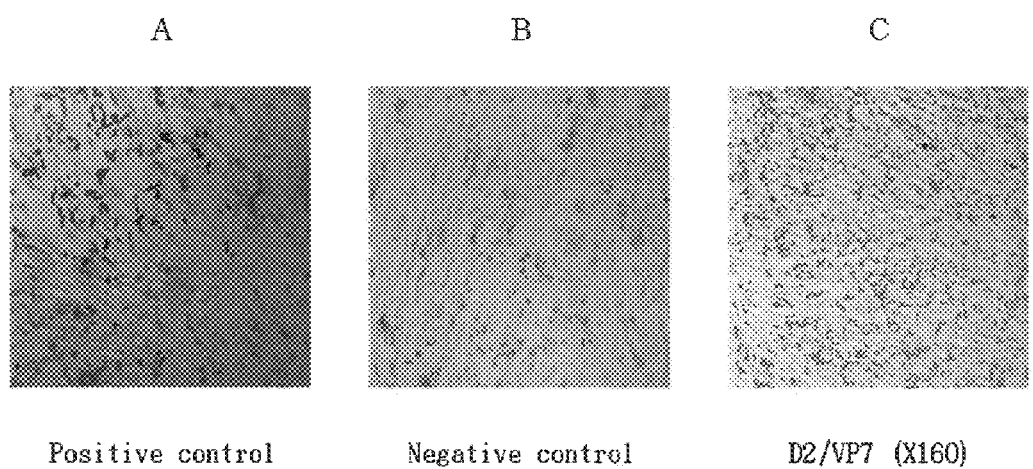

4. Neutralizing Antibody Producing Ability of Recombinant Antigen Complex Protein In order to identify whether the antibody specific for the recombinant antigen complex D2-VP7 has neutralizing effect for rotavirus and hepatitis A virus, cells were infected with each virus and cultured, and then were reacted with the antiserum against the recombinant antigen complex D2-VP7. It was identified that the antiserum has the neutralizing ability of inhibiting the viruses, with the cytopathic effect decreased to 320× dilution for rotavirus and to 160× dilution for hepatitis A virus, when compared with a positive control group (FIG. 7a and FIG. 7b). Table 2 shows the $TCID_{50}$ measurement result for the antiserum against the recombinant antigen complex D2-VP7 obtained by inoculating to a rabbit.

TABLE 2

|  | Human rotavirus | Hepatitis A virus |
|---|---|---|
| Titer ($TCID_{50}$) | $10^{-5.35}$/mL | $10^{-1.95}$/mL |

5. Electron Microscopic Image of Virus-Like Particle of Rotavirus

Figure 8:
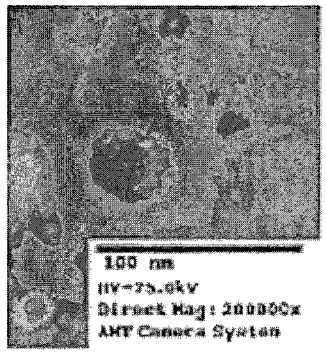
FIG. 8 shows a virus-like particle (VLP) of rotavirus comprising hepatitis A virus antigen. Panel A shows a virus-like particle of rotavirus comprising a recombinant antigen complex protein in which rotavirus proteins VP2, VP6 and VP4, and fusion protein in which hepatitis A virus antigen D2 and a rotavirus protein VP7 are linked, and panel B shows a core-like particle (CLP) of rotavirus comprising proteins of VP2 and VP6.
Figure 8:
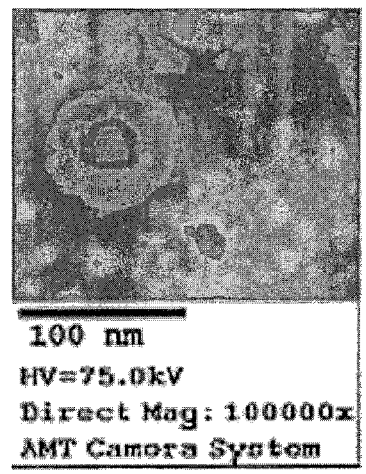
Figure 9:
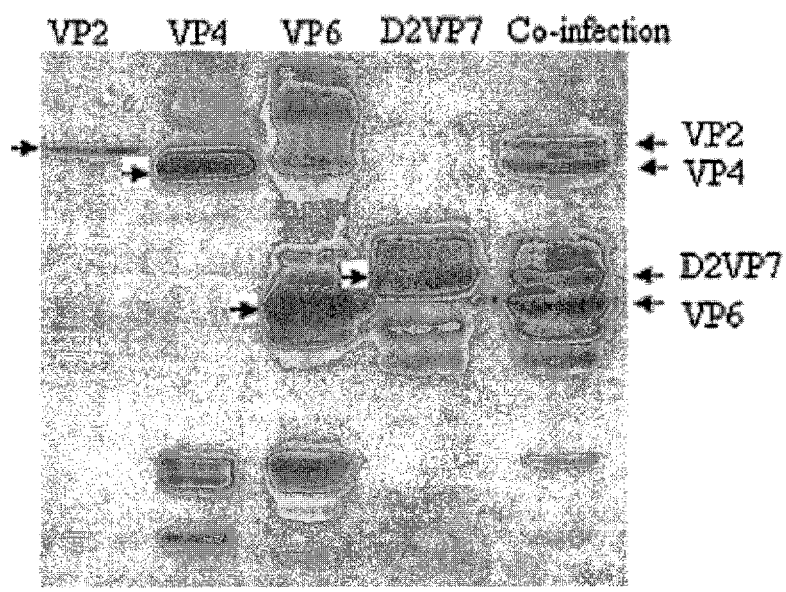
FIG. 9 shows a Western blot analysis result showing that a virus-like particle of rotavirus of the present disclosure is recognized by antibodies specific for rotavirus proteins VP2, VP4 and VP6 produced in a rabbit.

The synthesized virus-like particle of rotavirus was observed using an electron microscope. It was identified that the virus-like particle of rotavirus comprising the recombinant antigen complex D2-VP7 was formed successfully (FIG. 8).

6. Immunogenicity of Virus-Like Particle of Rotavirus

In order to investigate the immunogenicity of the virus-like particle of rotavirus, the virus-like particle was isolated by 10% SDS-PAGE and Western blot was carried out using rotavirus-specific antibody produced from a rabbit. Specific protein product corresponding to the size was identified (FIG.

Figure 10A:
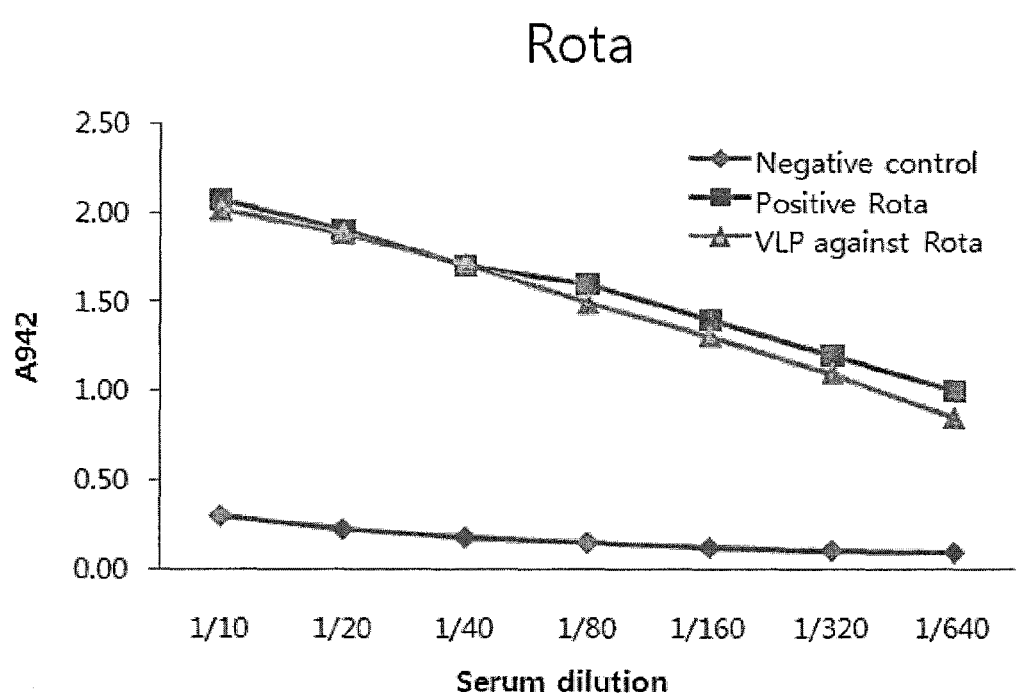
FIG. 10a and FIG. 10b show an immunogenicity evaluation result of a virus-like particle of rotavirus by ELISA. The VLP of rotavirus comprising a recombinant antigen complex protein D2-VP7 was injected to a mouse for immunization, and immunized serum isolated therefrom was subjected to antibody measurement.
Figure 10B:
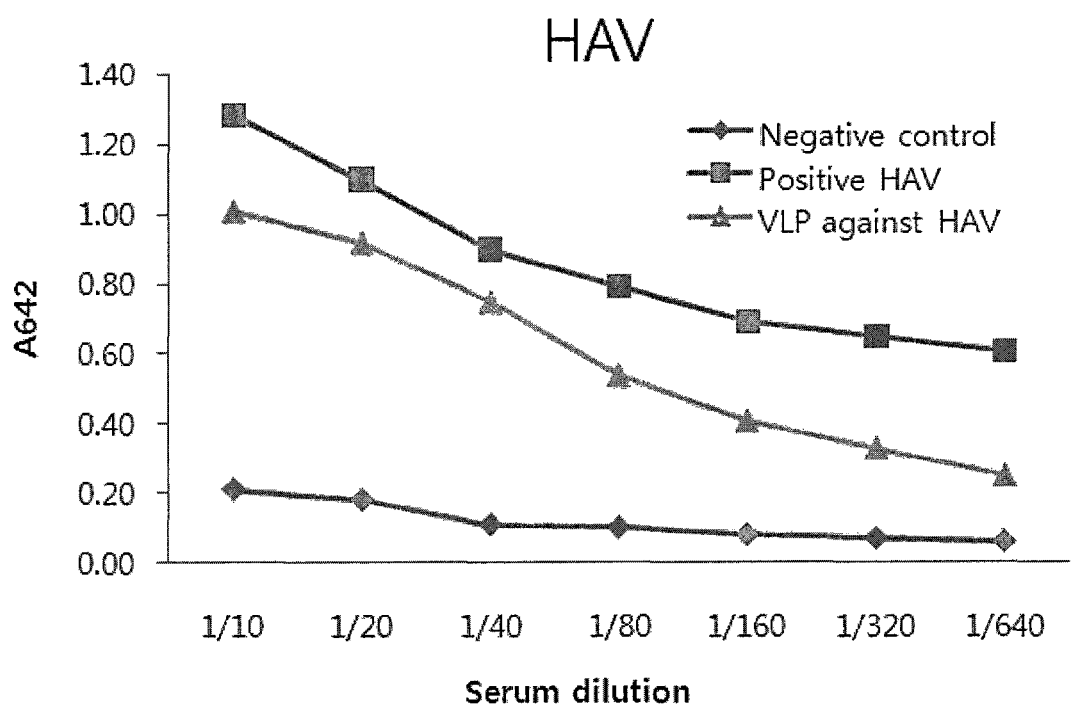

9). In order further confirm the immunogenicity of the virus-like particle of rotavirus, a mouse was immunized with the prepared virus-like particle and it was investigated whether antibody specific for the antigen is produced. Comparison with a negative control group revealed that the antibody specific for the virus was produced (FIG. 10).

7. Conclusion

In the present disclosure, baculovirus expression vector systems capable of expressing two recombinant antigen complex proteins D2-VP7 and D3-VP7 were constructed and the antigen complex proteins were expressed in insect Sf9 cells. The immunogenicity of the expressed recombinant antigen complex proteins was identified by Western blot analysis using rabbit and human patient serums. Furthermore, the recombinant antigen complex protein identified to have immunogenicity was directly injected into a rabbit and a serum obtained therefrom was subjected to ELISA analysis. Through production of the virus-specific antibody, its immunogenicity was reconfirmed. In addition, it was identified that the antiserum obtained from immunization of a rabbit has neutralizing antibody of inhibiting both hepatitis A virus and rotavirus. Furthermore, when a mouse was immunized with the virus-like particle of rotavirus comprising the rotavirus-hepatitis A virus recombinant antigen complex, antibodies specific for hepatitis A virus and rotavirus were produced.

Accordingly, the antigen complex protein expression system of the present disclosure may be utilized for spontaneous and large-scale expression of hepatitis A virus- and rotavirus-derived antigen proteins, synthesis of chimeric virus-like particles, development of complex vaccines for hepatitis A virus and rotavirus, and development of complex virus-like particle vaccines comprising various viral antigen.

While the present disclosure has been described with respect to the specific embodiments, it will be apparent to those skilled in the art that various changes and modifications may be made without departing from the spirit and scope of the disclosure as defined in the following claims.

The present disclosure provides a construct for expressing a rotavirus antigen complex loaded with a heterologous virus epitope, a vaccine composition comprising the rotavirus antigen complex, a virus-like particle of rotavirus comprising the rotavirus antigen complex, and a vaccine composition comprising the virus-like particle of rotavirus. According to the present disclosure, an antigen complex comprising a rotavirus antigen as well as a heterologous virus epitope and a virus-like particle of rotavirus comprising the antigen complex can be produced in large scale at low cost. Thus, the present disclosure may be applied for research and development of novel complex vaccines for rotavirus and heterologous virus.

What is claimed is:

1. A virus-like particle of rotavirus comprising: (i) polypeptides of VP2, VP4 and VP6 of rotavirus; and (ii) a rotavirus antigen complex in which hepatitis A virus domain 2 (D2; SEQ ID NO:2) or domain 3 (D3; SEQ ID NO:3) and rotavirus VP7 (SEQ ID NO:1) are linked.

2. A vaccine composition comprising the virus-like particle of rotavirus of claim 1.

3. The virus-like particle of rotavirus according to claim 1, wherein the rotavirus VP7 and the hepatitis A virus D2 or D3 are linked by a peptide linker of Leu-Glu-Pro-Gly or Lys-Asp-Glu-Leu.

4. The virus-like particle of rotavirus of claim 1, comprising hepatitis A virus D2.

5. The virus-like particle of rotavirus of claim 1, comprising hepatitis A virus D3.

* * * * *